(12) United States Patent
Weerasooriya et al.

(10) Patent No.: US 8,841,241 B2
(45) Date of Patent: Sep. 23, 2014

(54) ANIONIC POLYALKOXY GROUP COMPRISING SURFACTANTS ON BASIS OF GUERBET-ALCOHOLS, METHOD OF MANUFACTURE AND USE IN ENHANCED OIL RECOVERY (EOR) APPLICATIONS

(75) Inventors: Upali P. Weerasooriya, Austin, TX (US); Gary A. Pope, Cedar Park, TX (US); Christian Bittner, Bensheim (DE); Guenter Oetter, Frankenthal (DE); Jack F. Tinsley, Mannheim (DE); Christian Spindler, Ludwigshafen (DE); Gabriela Alvarez-Jurgenson, Mannheim (DE); Sophie Maitro-Vogel, Mannheim (DE)

(73) Assignees: Board of Regents, The University of Texas System, Austin, TX (US); BASF SE, Ludwigshafen (DE)

( * ) Notice: Subject to any disclaimer, the term of this patent is extended or adjusted under 35 U.S.C. 154(b) by 514 days.

(21) Appl. No.: 13/085,248

(22) Filed: Apr. 12, 2011

(65) Prior Publication Data

US 2011/0281779 A1    Nov. 17, 2011

Related U.S. Application Data

(60) Provisional application No. 61/325,015, filed on Apr. 16, 2010.

(51) Int. Cl.
*C09K 8/584* (2006.01)
*E21B 43/16* (2006.01)

(52) U.S. Cl.
USPC .......................... 507/246; 507/244; 166/802

(58) Field of Classification Search
None
See application file for complete search history.

(56) References Cited

U.S. PATENT DOCUMENTS

| | | | |
|---|---|---|---|
| 5,092,405 A | | 3/1992 | Prukop |
| 6,342,473 B1 * | | 1/2002 | Kott et al. .................. 510/357 |
| 7,119,125 B1 * | | 10/2006 | O'Lenick et al. ............. 516/25 |
| 7,985,718 B2 | | 7/2011 | Steinbrenner et al. |
| 7,989,399 B2 | | 8/2011 | Stoian et al. |
| 2008/0217604 A1 | | 9/2008 | Yokoyama et al. |
| 2010/0280162 A1 | | 11/2010 | Stesikova et al. |
| 2011/0220353 A1 | | 9/2011 | Bittner et al. |
| 2011/0220364 A1 | | 9/2011 | Bittner et al. |
| 2011/0220365 A1 | | 9/2011 | Bittner et al. |
| 2011/0220366 A1 | | 9/2011 | Bittner et al. |

FOREIGN PATENT DOCUMENTS

| | | |
|---|---|---|
| AU | 2011240606 B2 | 10/2011 |
| EP | 0167337 A2 | 1/1986 |
| EP | 1022326 A1 | 7/2000 |
| WO | 2000/043476 A2 | 7/2000 |
| WO | 2011/037975 A2 | 3/2011 |
| WO | 2011130310 | 10/2011 |

OTHER PUBLICATIONS

International Search Report and Written Opinion for PCT/US2011/032166, dated Jun. 16, 2011, 15 pages.
O'Lenick, Jr., Anthony J. "Guerbet Chemistry" Journal of Surfactants and Detergents, Springer, Berlin, DE, vol. 4, No. 3, Jul. 1, 2001, pp. 311-315.
European Patent Office, Supplementary European Search Report for Application No. 117969466.1 (PCT/US2011032166) dated Aug. 21, 2013, 10 pp.
The Eurasian Patent Organization (EAPO), Office Action dated Dec. 12, 2013 for Eurasia Patent Application No. 201270743 (with English translation), 6 pp.

* cited by examiner

*Primary Examiner* — Susannah Chung
*Assistant Examiner* — Kumar R Bhushan
(74) *Attorney, Agent, or Firm* — Edwin S. Flores; Chalker Flores, LLP

(57) ABSTRACT

Compositions and methods of synthesis of anionic surfactants by alkoxylation of a Guerbet alcohol (GA) having 12 to 36 carbon atoms using butylene oxide, and optionally propylene oxide and/or ethylene oxide followed by the incorporation of a terminal anionic group are described herein. The GA of the present invention is made by a facile and inexpensive method that involves high temperature base catalyzed dimerization of alcohols with 6 to 18 carbon atoms. The large hydrophobe ether surfactants of the present invention find uses in enhanced oil recovery (EOR) applications where it is used for solubilization and mobilization of oil and for environmental cleanup. Further, the hydrophobe alkoxylated GA without anionic terminal group can be used as an ultra-high molecular weight non-ionic surfactant.

35 Claims, 2 Drawing Sheets

0.33% C32-7PO-10EO-SO4, 0.33% C15-18 IOS, 0.33% C32-7BO-7PO-25EO-SO4, 0.5% TEGBE, 3.75% EDTA Na₄

0.33% C32-7PO-10EO-SO4, 0.33% C15-18 IOS, 0.58% C32-7BO-7PO-25EO-SO4, 0.5% TEGBE, 3.75% EDTA Na₄

ANIONIC POLYALKOXY GROUP COMPRISING SURFACTANTS ON BASIS OF GUERBET-ALCOHOLS, METHOD OF MANUFACTURE AND USE IN ENHANCED OIL RECOVERY (EOR) APPLICATIONS

CROSS-REFERENCE TO RELATED APPLICATIONS

This patent application is a non-provisional application of U.S. provisional patent application 61/325,015 filed on Apr. 16, 2010 and entitled "Novel Anionic Polyalkoxy Group Comprising Surfactants on Basis of Guerbet-Alcohols, Method of Manufacture and Use in Enhanced Oil Recovery (EOR) Applications" which is hereby incorporated by reference in its entirety.

TECHNICAL FIELD OF THE INVENTION

The present invention relates in general to the field of oil recovery, and more particularly, to a method of transforming a long chain branched hydrophobe alcohol of the Guerbet Alcohol (GA) type to anionic surfactants and methods of using the compositions manufactured by this method for enhanced oil recovery (EOR) applications.

STATEMENT OF FEDERALLY FUNDED RESEARCH

None.

REFERENCE TO A SEQUENCE LISTING

None.

BACKGROUND OF THE INVENTION

Without limiting the scope of the invention, its background is described in connection with methods of manufacture and use of Guerbet alcohols for oil recovery applications, in particular enhanced oil recovery (EOR).

In natural mineral oil deposits, mineral oil is present in the cavities of porous reservoir rocks which are closed off from the earth's surface by impervious covering strata. The cavities may be very fine cavities, capillaries, pores or the like. Fine pore necks may have, for example, a diameter of only about 1 µm. In addition to mineral oil, including proportions of natural gas, a deposit contains water having a higher or lower salt content.

In mineral oil production, a distinction is made between primary, secondary and tertiary production.

In primary production, after drilling into the deposit, the mineral oil flows by itself under the autogenous pressure of the deposit through the well to the surface.

After primary production, the secondary production is therefore used. In secondary production, in addition to the wells which serve the production of the mineral oil, the so-called production wells, further wells are drilled into the mineral oil-carrying formation. Water is forced through these so-called injection wells into the deposit in order to maintain the pressure or to increase it again. By forcing in water, the mineral oil is slowly forced through the cavities in the formation, starting from the injection well, in the direction of the production well. However, this functions only as long as the cavities are completely filled with oil and the more viscous oil is pushed ahead by the water. As soon as the low-viscosity water breaks through cavities, it flows from this time onward along the path of least resistance, i.e. through the resulting channel, and no longer pushes the oil in front of it.

As a rule, only about 30 to 35% of the amount of mineral oil present in the deposit can be extracted by means of primary and secondary production.

It is known that the mineral oil yield can be further increased by tertiary oil production measures (also known as enhanced oil recovery, EOR). An overview of tertiary oil production is to be found, for example, in Journal of Petroleum Science and Engineering 19 (1998) 265-280. Tertiary oil production includes thermal processes in which hot water or superheated steam is forced into the deposit. As a result of this, the viscosity of the oil is reduced. Gases, such as $CO_2$ and nitrogen, can also be used as a flooding medium.

Tertiary oil production furthermore includes processes in which suitable chemicals are used as assistants for oil production. The situation toward the end of the water flood can be influenced by these and mineral oil held in the rock formation up to that time can also be extracted thereby.

For example, the interfacial tension a between the mineral oil and the aqueous phase can be reduced by the addition of suitable surfactants. This technique is also known as "surfactant flooding". In particular, surfactants which can reduce σ to values of $<10^{-2}$ mN/m (ultralow interfacial tension) are suitable for this purpose. In this way, the oil droplets are able to change their shape and can be forced through the capillary openings by the flood water.

The oil droplets can then combine to form a continuous oil layer. This has advantages in two respects: firstly, when the continuous oil layer advances through new porous rock, the oil droplets present there can coalesce with the layer. Furthermore, the oil-water interface is substantially reduced by the combination of the oil droplets to form an oil layer, and surfactant no longer required is therefore released. The surfactant released can then mobilize oil droplets remaining in the formation.

The requirements regarding surfactants for tertiary mineral oil productions differ substantially from requirements regarding surfactants for other applications: suitable surfactants for tertiary mineral oil production should reduce the interfacial tension between water and oil (usually about 20 mN/m) to particularly low values of less than $10^{-2}$ mN/m in order to permit sufficient mobilization of the mineral oil. This must take place at the usual deposit temperatures of about 15° C. to about 130° C. and in the presence of water having a high salt content, in particular also in the presence of high proportions of calcium and/or magnesium ions; the surfactants must therefore also be soluble in reservoir water having a high salt content.

U.S. Pat. No. 5,092,405 issued to Prukop (1992) discloses a method of recovering heavy oil from an underground reservoir by surfactant flooding which comprises injecting an aqueous surfactant solution comprising about 0.1% to about 5% by weight of an alkoxylated nonionic or ionic surfactant through an injection well into an underground reservoir containing a heavy oil having an average API gravity below about 20° and a reservoir temperature above about 65.6° F. According to the Prukop patent, the alkoxylated surfactant must have sufficient alkylene oxide groups comprised of ethylene oxide or propylene oxide to have a cloud point above about 37.8° F. and below reservoir temperature, and be water-soluble in the surfactant solution to be injected at a temperature below its cloud point, and have a sufficiently large hydrophobe to be soluble in the reservoir's heavy oil at a temperature equal to or greater than reservoir temperature.

U.S. Pat. No. 7,119,125 issued to O'Lenick et al. (2006) relates to specific compositions made by the sulfation of alkoxylated crude $C_{12}$ to $C_{40}$ Guerbet alcohol mixtures that contain between 15% and 50% lower molecular weight alkoxylated alcohols. The polyalkoxy groups comprise ethylene oxide and/or propylene oxide units. According to the '125 patent the lower molecular weight alcohols are the raw material alcohols used to make the Guerbet. Sulfated compositions made from this specific bi-modal distribution have unique emulsification properties and experience minimal chromatographic separation when used in downhole applications. It is suggested to use said mixtures for enhanced oil recovery. However emulsification of crude oil is difficult due to low shear forces in the reservoir.

U.S. Patent Application No. 20080217064 (Stoian and Smith, 2008) discloses a drilling fluid comprising: a non-ionic surfactant including at least one of a branched alcohol ethoxylate and a capped alcohol ethoxylate, a detergent builder and a viscosifier. The non-ionic surfactant includes alkyl polyethylene glycol ethers based on C10-Guerbet alcohol and ethylene oxide.

U.S. Patent Application No. 20090270281 (Steinbrenner et al., 2009) describes the use of a surfactant mixture comprising at least one surfactant having a hydrocarbon radical composed of from 12 to 30 carbon atoms and at least one cosurfactant having a branched hydrocarbon radical composed of from 6 to 11 carbon atoms for tertiary mineral oil extraction. According to the Steinbrenner invention, the surfactants (A) are used in a mixture with at least one cosurfactant (B) which has the general formula $R^2$—O—$(R^3$—O$)_n$—$R^4$, where the $R^2$, $R^3$ and $R^4$ radicals and the number n are each defined as follows: n is from 2 to 20, $R^2$ is a branched hydrocarbon radical which has from 6 to 11 carbon atoms and an average degree of branching of from 1 to 2.5, $R^3$ are each independently an ethylene group or a propylene group, with the proviso that the ethylene and propylene groups—where both types of groups are present—may be arranged randomly, alternately or in block structure, $R^4$ is hydrogen or a group selected from the group of —$SO_3H$, —$PO_3H_2$, —$R^5$—COOH, —$R^5$—$SO_3H$ or —$R^5$—$PO_3H_2$ or salts thereof, where $R^5$ is a divalent hydrocarbon group having from 1 to 4 carbon atoms.

SUMMARY OF THE INVENTION

The present invention discloses compositions, methods of synthesis, and applications of surfactants comprising both, terminal anionic groups and polyether groups. The surfactants described herein and made by a facile and inexpensive process from long-chain a branched hydrophobe alcohols of Guerbet alcohol (GA) structure. The GA is alkoxylated with poly butylene oxide groups (BO), poly propylene oxide groups (PO) and/or poly ethylene oxide groups (EO) added on followed by an anionic group (e.g. a sulfate group) to yield the anionic ether surfactants of the present invention.

The present invention in one embodiment provides an anionic ether surfactant comprising a branched hydrophobic group derived from a Guerbet alcohol (GA) with one or more poly butoxy groups (BO), poly propoxy groups (PO) and/or poly ethoxy groups (EO) and an anionic group formula (I), $$R^1O—BO_x—PO_y\text{-}EO_z—X—Y^{a-} a/bM^{b+} \qquad (I),$$

wherein $R^1$ corresponds to an aliphatic, branched hydrocarbon group $C_nH_{2n+1}$ derived from a Guerbet alcohol (GA) wherein n corresponds to the number of carbon atoms and ranges from 12 to 36, wherein BO corresponds to a butoxy group, wherein x corresponds to the number of butoxy groups and ranges from 2 to 25, wherein PO corresponds to a propoxy group, wherein y corresponds to the number of propoxy groups and ranges from 0 to 25, wherein EO corresponds to a ethoxy group, wherein z corresponds to the number of ethoxy groups and ranges from 0 to 70, wherein the sum of y+z ranges preferably from 5 to 105; wherein X is selected from a single bond, an alkylene group with 1 to 10 carbon atoms or an alkenylene group with 2 to 10 carbon atoms, wherein Y is an anionic group selected from the group of sulfate groups, sulfonate groups, carboxylate groups, phosphate groups or phosphonate groups, and M is the counter ion to the anionic group, wherein a corresponds to a number of 1 or 2 and b corresponds to a number of from 1 to 3. The number of carbon atoms, n, is 12, 13, 14, 15, 16, 17, 18, 19, 20, 21, 22, 23, 24, 25, 26, 27, 28, 29, 30, 31, 32, 33, 34, 35, and 36. In related aspects of the composition of the present invention x is 2, 3, 4, 8, 12, 16, 20, 22, 23, 24, and 25, y is 0, 2, 4, 6, 8, 11, 14, 17, 21, and 25, and z is 6, 8, 10, 12, 16, 20, 24, 32, 40, 48, 53, 57, 59, 62, 66, and 70. Preferably, the counter ion is selected from the group of $H^+$, $Na^+$, $K^+$, $Mg^+$, $Ca^{2+}$, and $NH_4^+$. In yet another aspects, the anionic surfactant has a formula $R^1O—BO_7—PO_7\text{-}EO_{25}—SO_3^-$ $Na^+$. In yet another embodiment, the anionic surfactant has a formula $R^1O—BO_7—PO_7\text{-}EO_{25}—SO_3^-$ $NH_4^+$. In a specific aspect the anionic ether surfactant has a formula $R^1O—BO_7—PO_7\text{-}EO_{25}—SO_3^-1/b$ $M^{b+}$, wherein $R^1$ is a hydrocarbon group $C_{32}H_{65}$—.

In another embodiment the present invention discloses a method for making an anionic surfactant of formula (I)

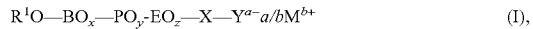

$$R^1O—BO_x—PO_y\text{-}EO_z—X—Y^{a-}a/bM^{b+} \qquad (I),$$

from one or more branched Guerbet Alcohols (GA) comprising the steps of providing one or more Guerbet Alcohols (GA) having the general formula $R^1$—OH by dimerizing one or more alcohols $R^2$—OH in the presence of a base at a temperature from 175° C. to 275° C., wherein $R^2$ is an aliphatic, linear or branched alcohol and wherein the number of carbon atoms in $R^2$ is from 6 to 18, butoxylating the one or more GA with x butylene oxide (BO) units to form a butoxylated GA, alkoxylating the one or more butoxylated GA with y propylene oxide (PO) units and z ethylene oxide (EO) units or both; and converting the terminal OH-group of the alkoxylated GA thus obtained to the terminal group —X—$Y^{a-}$ a/b $M^{b+}$. The $R^1$ of the anionic ether surfactant of formula (I) corresponds to an aliphatic, branched hydrocarbon group $C_nH_{2n+1}$ derived from a Guerbet alcohol (GA) wherein n corresponds to the number of carbon atoms and ranges from 12 to 36. BO corresponds to a butoxy group, wherein x corresponds to the number of butoxy groups and ranges from 2 to 25, wherein PO corresponds to a propoxy group, wherein y corresponds to the number of propoxy groups and ranges from 0 to 25, wherein EO corresponds to a ethoxy group, wherein z corresponds to the number of ethoxy groups and ranges from 0 to 70, wherein the sum of y+z ranges preferably from 5 to 105. X is selected from a single bond, an alkylene group with 1 to 10 carbon atoms or an alkenylene group with 2 to 10 carbon atoms, Y is an anionic group selected from the group of sulfate groups, sulfonate groups, carboxylate groups, phosphate groups or phosphonate groups, and M is the counter ion to the anionic group, wherein a corresponds to a number of 1 or 2 and b corresponds to a number of from 1 to 3. In related aspects the number of carbon atoms, n, is 12, 13, 14, 15, 16, 17, 18, 19, 20, 21, 22, 23, 24, 25, 26, 27, 28, 29, 30, 31, 32, 33, 34, 35, and 36, x is 2, 3, 4, 8, 12, 16, 20, 22, 23, 24, and 25, y is 0, 2, 4, 6, 8, 11, 14, 17, 21, and 25, and z is 6, 8, 10, 12, 16, 20, 24, 32, 40, 48, 53, 57, 59, 62, 66, and 70. In one aspect the counter ion is selected from the group of $H^+$, $Na^+$, $K^+$, $Mg^+$, $Ca^{2+}$, and $NH_4^+$. In a specific aspect the anionic ether surfactant has a formula $R^1O—BO_7—PO_7\text{-}EO_{25}—SO_3^-$ 1/b $M^{b+}$, wherein $R^1$ is a hydrocarbon group $C_{32}H_{65}$—.

In another aspect the yield in course of the Guerbet reaction is 85% to less than 100%, thus obtaining a mixture which comprises the Guerbet Alcohol $R^1$—OH with the remainder comprising the monomer alcohol $R^2$—OH and wherein the mixture thus obtained is used for the alkoxylation following the Guerbet condensation. The base used in the Guerbet reaction of the method of the present invention comprises NaOH or KOH. In yet another aspect the yield of the GA hydrophobe made according to the method of the present invention is 85%, 86%, 87%, 88%, 89%, 90%, 91%, 92%, 93%, 94%, 95%, 96%, 97%, 98%, and 99%. The Guerbet reaction as detailed in the method of the present invention is carried out preferably at a temperature range of about 175° C. to 275° C. and the GA is branched at near mid-point of the carbon chain. In one aspect the Guerbet reaction is carried out at 175° C., 190° C., 200° C., 220° C., 230° C., 240° C., 250° C., and 275° C. In a specific aspect the dimerization via the Guerbet reaction is carried out at 230° C.

In yet another embodiment the present invention describes a composition for enhanced oil recovery (EOR), environmental ground water cleanup, and other surfactant based operations comprising: at least one or more surfactants, wherein at least one or more of the surfactants have a general formula (I), one or more alkalinity generating agents, and a solvent; wherein the one or more anionic ether surfactants, the one or more alkalinity generating agents are dissolved in the solvent

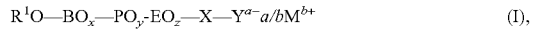

$$R^1O-BO_x-PO_y-EO_z-X-Y^{a-}{}_{a/b}M^{b+} \quad (I),$$

wherein $R^1$, X, Y, M, n, x, y, z, a, b are described herein below.

$R^1$ corresponds to an aliphatic, branched hydrocarbon group $C_nH_{2n+1}$ derived from a Guerbet alcohol (GA) wherein n corresponds to the number of carbon atoms and ranges from 12 to 36. BO corresponds to a butoxy group, wherein x corresponds to the number of butoxy groups and ranges from 2 to 25, PO corresponds to a propoxy group, wherein y corresponds to the number of propoxy groups and ranges from 0 to 25, EO corresponds to a ethoxy group, wherein z corresponds to the number of ethoxy groups and ranges from 0 to 70. The sum of y+z ranges preferably from 5 to 105. X is selected from a single bond, an alkylene group with 1 to 10 carbon atoms or an alkenylene group with 2 to 10 carbon atoms, Y is an anionic group selected from the group of sulfate groups, sulfonate groups, carboxylate groups, phosphate groups or phosphonate groups, and M is the counter ion to the anionic group, wherein a corresponds to a number of 1 or 2 and b corresponds to a number of from 1 to 3. The number of carbon atoms, n, is 12, 13, 14, 15, 16, 17, 18, 19, 20, 21, 22, 23, 24, 25, 26, 27, 28, 29, 30, 31, 32, 33, 34, 35, and 36. In related aspects of the composition of the present invention x is 2, 3, 4, 8, 12, 16, 20, 22, 23, 24, and 25, y is 0, 2, 4, 6, 8, 11, 14, 17, 21, and 25, and z is 6, 8, 10, 12, 16, 20, 24, 32, 40, 48, 53, 57, 59, 62, 66, and 70.

In one aspect the counter ion is selected from the group of $H^+$, $Na^+$, $K^+$, $Mg^+$, $Ca^{2+}$, and $NH_4^+$. In another aspect the one or more anionic ether surfactants of formula (I) are selected from the group consisting of $C_{32}H_{65}O$—$BO_7$—$PO_7$-$EO_{25}$—$SO_3^-$ 1/b $M^{b+}$, $C_{32}H_{65}O$—$PO_7$-$EO_6$—$SO_3^-$ 1/b $M^{b+}$, $C_nH_{2n+1}O$-$EO_3$—$SO_3^-$ 1/b $M^{b+}$ with n=12 to 15, $C_nH_{2n+1}O$-$EO_{12}$—$SO_3^-$ 1/b $M^{b+}$ with n=12 to 15, $C_nH_{2n+1}O$—$PO_7$—$SO_3^-$ 1/b $M^{b+}$ with n=16 to 18, $C_nH_{2n+1}O$—$PO_7$-$EO_5$—$SO_3^-$ 1/b $M^{b+}$ with n=16 to 17, $C_{13}H_{27}O$—$PO_7$—$SO_3^-$ 1/b $M^{b+}$, $C_{20}H_{41}O$—$PO_7$-$EO_{10}$—$SO_3^-$ 1/b $M^{b+}$. In yet another aspect the solvent comprises water, hard brine, hard water, polymer containing solutions, or any combinations thereof.

In one aspect the composition comprises additionally one or more alkalinity generating agents comprise alkali earth metal hydroxides, NaOH, KOH, LiOH, ammonia, $Na_2CO_3$, $NaHCO_3$, Na-metaborate, sodium silicate, sodium orthosilicate, with or without $EDTANa_4$, other polycarboxylates or any combinations thereof. In another aspect the composition furthermore comprises cosurfactants selected from sulfate, sulfonate, carboxylate anion based surfactants, ether sulfates, ethoxy sulfates, propoxy sulfates, perfluorooctanoate (PFOA or PFO), perfluorooctanesulfonate (PFOS), sodium dodecyl sulfate (SDS), ammonium lauryl sulfate, alkyl sulfate salts, sodium lauryl ether sulfate (SLES), alkyl benzene sulfonate, soaps, and fatty acid salts. In yet another aspect the composition of the present invention is used alone or in an alkaline-surfactant-polymer formulation for EOR applications and comprises 0.1%, 0.15%, 0.2%, 0.25% 0.3%, 0.35%, 0.4%, 0.45%, 0.5%, and so on of the one or more alkalinity generating agents.

Another embodiment of the present invention discloses a method of enhanced oil recovery from a hydrocarbon bearing formation comprising the steps of: injecting a composition comprising at least an anionic ether surfactant composition having a general formula (I)

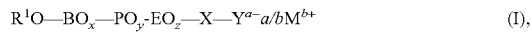

$$R^1O-BO_x-PO_y-EO_z-X-Y^{a-}{}_{a/b}M^{b+} \quad (I),$$

into the hydrocarbon bearing formation through at least one injection well and recovering crude oil from the formation through at least one production well. $R^1$, X, Y, M, n, x, y, z, a, b have been previously described hereinabove and are restated here. $R^1$ corresponds to an aliphatic, branched hydrocarbon group $C_nH_{2n+1}$ derived from a Guerbet alcohol (GA) wherein n corresponds to the number of carbon atoms and ranges from 12 to 36. BO corresponds to a butoxy group, wherein x corresponds to the number of butoxy groups and ranges from 2 to 25, PO corresponds to a propoxy group, wherein y corresponds to the number of propoxy groups and ranges from 0 to 25, EO corresponds to a ethoxy group, wherein z corresponds to the number of ethoxy groups and ranges from 0 to 70. The sum of y+z ranges preferably from 5 to 105. X is selected from a single bond, an alkylene group with 1 to 10 carbon atoms or an alkenylene group with 2 to 10 carbon atoms, Y is an anionic group selected from the group of sulfate groups, sulfonate groups, carboxylate groups, phosphate groups or phosphonate groups, and M is the counter ion to the anionic group, wherein a corresponds to a number of 1 or 2 and b corresponds to a number of from 1 to 3. The number of carbon atoms, n, is 12, 13, 14, 15, 16, 17, 18, 19, 20, 21, 22, 23, 24, 25, 26, 27, 28, 29, 30, 31, 32, 33, 34, 35, and 36. In related aspects of the composition of the present invention x is 2, 3, 4, 8, 12, 16, 20, 22, 23, 24, and 25, y is 0, 2, 4, 6, 8, 11, 14, 17, 21, and 25, and z is 6, 8, 10, 12, 16, 20, 24, 32, 40, 48, 53, 57, 59, 62, 66, and 70.

Preferably, after the injection of the surfactant composition a formulation comprising a thickening polymer is injected into the formation to recover the oil. In one aspect of the invention, the formation temperature is from 15° C. to 120° C. In another aspect of the invention, the concentration of all surfactants is from 0.05 to 5% by weight. In yet another aspect of the invention, the interfacial tension between the hydrocarbons and the water in the formation is reduced to less than 0.1 mN/m. In other aspects of the invention, the composition is an alkaline-surfactant-polymer formulation (ASP) and the composition used is the composition for enhanced oil recovery disclosed above.

In yet another embodiment the present invention describes a high molecular weight non-ionic surfactant composition comprising a branched hydrophobe alcohol selected from a Guerbet alcohol (GA) with more than one butoxy groups (BO), propoxy groups (PO), and ethoxy groups (EO) of formula (II)

$$R^1O—BO_x—PO_y\text{-}EO_z \quad (II)$$

wherein $R^1$ corresponds to an aliphatic, branched hydrocarbon group $C_nH_{2n+1}$ derived from a Guerbet alcohol (GA) wherein n corresponds to the number of carbon atoms and ranges from 12 to 36. BO corresponds to a butoxy group, wherein x corresponds to the number of butoxy groups and ranges from 2 to 25, PO corresponds to a propoxy group, wherein y corresponds to the number of propoxy groups and ranges from 0 to 25, EO corresponds to a ethoxy group, wherein z corresponds to the number of ethoxy groups and ranges from 0 to 70. The sum of y+z ranges preferably from 5 to 105.

The GA alcohol used to make the non-ionic surfactant of formula (II) may preferably be made by the method as previously described in the present invention. In one aspect the composition is used for enhanced oil recovery (EOR), environmental ground water cleanup, and other surfactant based applications.

In one embodiment the present invention provides a method for making a non-ionic surfactant of formula (II) from one or more highly branched Guerbet Alcohols (GA) comprising the steps of

$$R^1O—BO_x—PO_y\text{-}EO_z \quad (II)$$

wherein $R^1$ corresponds to an aliphatic, branched hydrocarbon group $C_nH_{2n+1}$ derived from a Guerbet alcohol (GA) wherein n corresponds to the number of carbon atoms and ranges from 12 to 36. BO corresponds to a butoxy group, wherein x corresponds to the number of butoxy groups and ranges from 2 to 25, PO corresponds to a propoxy group, wherein y corresponds to the number of propoxy groups and ranges from 0 to 25, EO corresponds to a ethoxy group, wherein z corresponds to the number of ethoxy groups and ranges from 0 to 70. The sum of y+z ranges preferably from 5 to 105.

The method as described in the instant invention comprises the steps of providing one or more Guerbet Alcohols (GA) having the general formula $R^1$—OH by dimerizing one or more alcohols $R^2$—OH in the presence of a base at a temperature from 175° C. to 275° C., wherein $R^2$ is an aliphatic, linear or branched alcohol and wherein the number of carbon atoms in $R^2$ is from 6 to 18, butoxylating the one or more GA with x butylene oxide (BO) units to form a butoxylated GA, alkoxylating the one or more butoxylated GA with y propylene oxide (PO) units and z ethylene oxide (EO) units or both.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
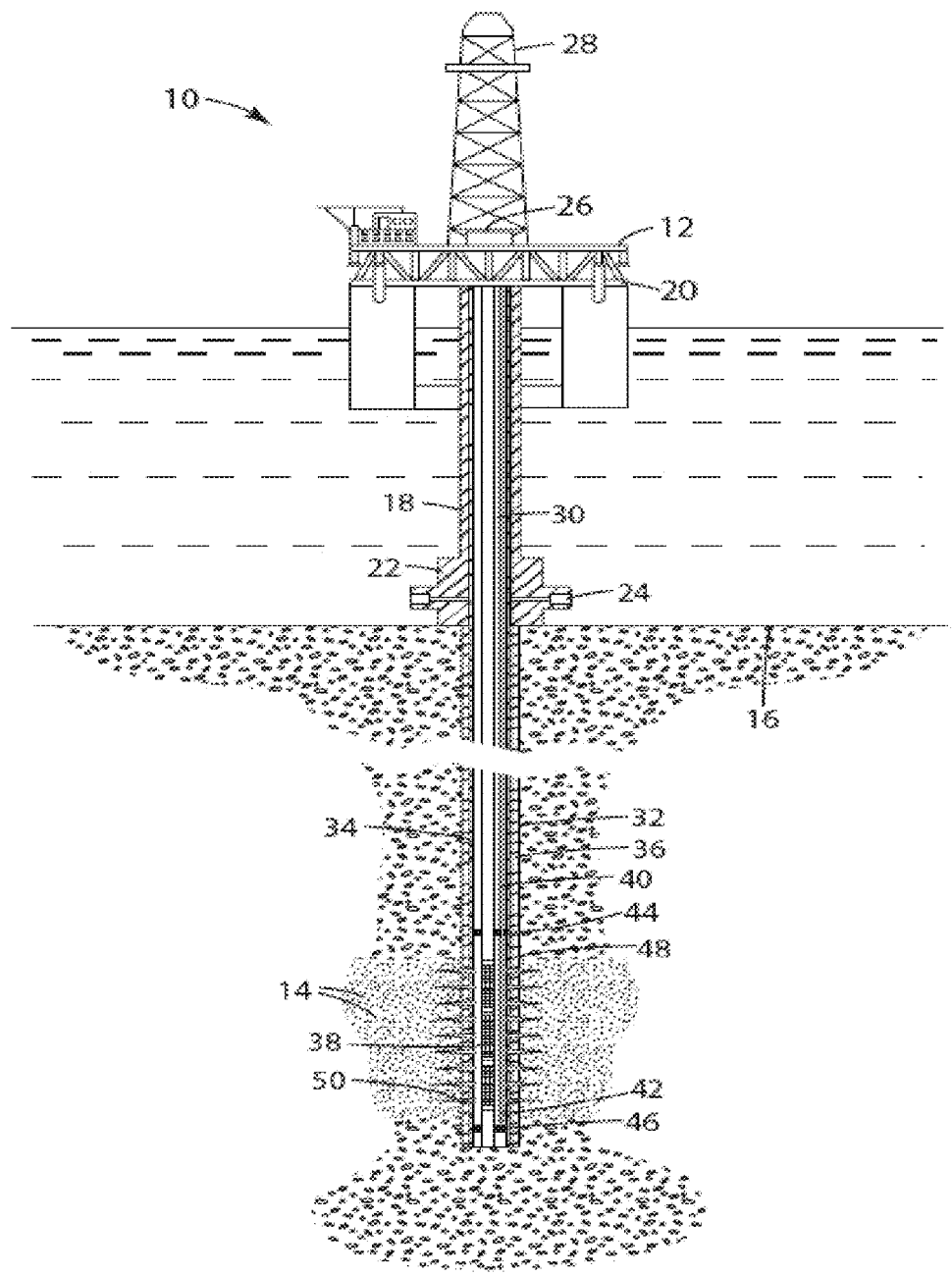
FIG. 1 is a schematic illustration of an offshore oil platform with facilities for injecting chemical solutions into the reservoir for the purpose of flooding the reservoir to enhance the oil recovery according to some embodiments of the present invention.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The following definitions of terms apply throughout the specification and claims.

For methods of treating a hydrocarbon-bearing formation and/or a well bore, the term "treating" includes placing a chemical (e.g., a fluorochemical, cationic polymer, or corrosion inhibitor) within a hydrocarbon-bearing formation using any suitable manner known in the art (e.g., pumping, injecting, pouring, releasing, displacing, spotting, or circulating the chemical into a well, well bore, or hydrocarbon-bearing formation).

The term "polymer" refers to a molecule having a structure that essentially includes the multiple repetitions of units derived, actually or conceptually, from molecules of low relative molecular mass. The term "polymer" includes "oligomer".

The term "bonded" refers to having at least one of covalent bonding, hydrogen bonding, ionic bonding, Van der Waals interactions, pi interactions, London forces, or electrostatic interactions.

The term "productivity" as applied to a well refers to the capacity of a well to produce hydrocarbons; that is, the ratio of the hydrocarbon flow rate to the pressure drop, where the pressure drop is the difference between the average reservoir pressure and the flowing bottom hole well pressure (i.e., flow per unit of driving force). This term is not pertinent to enhanced oil recovery. It applies to near wellbore treatments such as the 3M treatment, but here the idea is to flood the entire reservoir with chemical solutions to mobilize and displace the oil to the production wells.

"Alkyl group" and the prefix "alk-" are inclusive of both straight chain and branched chain groups and of cyclic groups having up to 30 carbons (in some embodiments, up to 20, 15, 12, 10, 8, 7, 6, or 5 carbons) unless otherwise specified. Cyclic groups can be monocyclic or polycyclic and, in some embodiments, have from 3 to 10 ring carbon atoms.

"Alkylene" is the divalent form of the "alkyl" groups defined above.

"Arylalkylene" refers to an "alkylene" moiety to which an aryl group is attached.

The term "aryl" as used herein includes carbocyclic aromatic rings or ring systems, for example, having 1, 2, or 3 rings and optionally containing at least one heteroatom (e.g., O, S, or N) in the ring. Examples of aryl groups include phenyl, naphthyl, biphenyl, fluorenyl as well as furyl, thienyl, pyridyl, quinolinyl, isoquinolinyl, indolyl, isoindolyl, triazolyl, pyrrolyl, tetrazolyl, imidazolyl, pyrazolyl, oxazolyl, and thiazolyl.

"Arylene" is the divalent form of the "aryl" groups defined above.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

The present invention describes a novel surfactant for enhanced oil recovery (EOR) applications. The composition described herein comprises an anionic surfactant based on a branched hydrophobe alcohol of the Guerbet alcohol (GA) type with poly butylene oxide groups (BO), poly propylene oxide groups (PO), poly ethylene oxide groups (EO) added on followed by an anionic group with may be linked to the polyalkoxy group by a suitable spacer group.

The molecules described hereinabove have applications in formulations for EOR, including but not limited to ASP formulations for EOR. The ultra large hydrophobe of the GA is further supplemented by the BO block and to some extent by the PO block. The large hydrophobicity may be balanced by an EO block of the ether sulfate to reach a desired hydrophilic-lipophilic balance (HLB) for the surfactant. Furthermore, the alkoxylated GA without anionic group can be used as an ultra-high molecular weight non-ionic surfactants The anionic ether surfactants of the present invention have the general formula (I)

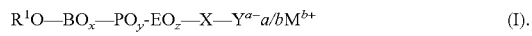

$$R^1O\text{—}BO_x\text{—}PO_y\text{-}EO_z\text{—}X\text{—}Y^{a-}{}_{a/b}M^{b+} \quad (I).$$

In formula (I) $R^1$ corresponds to an aliphatic, branched hydrocarbon group $C_nH_{2n+1}$ derived from a Guerbet alcohol (GA). The specific characteristics of Guerbet alcohol groups are disclosed below. In formula (I) n corresponds to the number of carbon atoms and ranges from 12 to 36. The number of carbon atoms, n, is 12, 13, 14, 15, 16, 17, 18, 19, 20, 21, 22, 23, 24, 25, 26, 27, 28, 29, 30, 31, 32, 33, 34, 35, and 36. Preferably, n ranges from 16 to 36, more preferably from 32 to 36. In particular n is a number selected from 32, 34, or 36 and most preferred n is 32.

In formula (I) BO corresponds to butoxy groups, PO corresponds to propoxy groups, and EO corresponds to ethoxy groups, which are arranged in block structure in the order indicated in formula (I), i.e. the surfactant comprises a poly butoxy block, and a poly propoxy block and/or a poly ethoxy block. The transition between the blocks may be abrupt or continuous.

In formula (I) x corresponds to the number of butoxy groups and ranges from 2 to 25, preferably from 2 to 15 and most preferred from 2 to 10. Specific examples of x include 2, 3, 4, 8, 12, 16, 20, 22, 23, 24, and 25.

y corresponds to the number of propoxy groups and ranges from 0 to 25, i.e. the presence of propoxy groups is only optional. Preferably, y ranges from 1 to 15 and most preferred from 5 to 9. Specific examples of y include 0, 2, 4, 6, 8, 11, 14, 17, 21, and 25.

z corresponds to the number of ethoxy groups and ranges from 0 to 70, i.e. ethoxy groups are only optional. Preferably, z ranges from 0 to 25 and most preferred from 1 to 15. Specific examples of y include 0, 6, 8, 10, 12, 16, 20, 24, 32, 40, 48, 53, 57, 59, 62, 66, and 70.

Furthermore, in a preferred embodiment of the invention, the sum of x+y ranges from 5 to 105, preferably from 5 to 25, and most preferred from 10 to 18.

Furthermore, in formula (I) $Y^{a-}$ is an anionic group selected from the group of sulfate groups —$OSO_3^-$, sulfonate groups —$SO_3^-$, carboxylate groups —$COO^-$, phosphate groups —$OP(O)(OH)_2^{2-}$ or phosphonate groups $\beta P(O)$ $(OH)_2^{2-}$. The number a represents the charge of the anionic groups and corresponds to a number of 1 or 2.

$M^{b+}$ is the counter ion to the anionic group. The number b represents the charge of the corresponding cation and corresponds to a number of 1 to 3. Basically, the cation may be any cation that does not render the surfactant insoluble for the intended use. Preferably, the cation may be selected from alkali metal ions, earth alkali metal ions, and ammonium ions $NR_4^+$, wherein each R represents H or a hydrocarbon group, in particular aliphatic hydrocarbon groups with 1 to 4 carbon atoms which optionally may be substituted by OH-groups. Preferably, the counter ion is selected from the group of $H^+$, $Na^+$, $K^+$, $Mg^+$, $Ca^{2+}$ and $NH_4^+$, and most preferably the counter ion is selected from $Na^+$ or $K^+$.

Preferably, the anionic groups are selected from the group of sulfate groups —$OSO_3^-$, sulfonate groups —$SO_3^-$, or carboxylate groups —$COO^-$, and most preferred are sulfate groups —$OSO_3^-$.

X is a linker or spacer joining the polyalkoxy group —$BO_x$—$PO_y$-$EO_z$— and the anionic group $Y^{a-}$ which is selected from a single bond or an alkylene group with 1 to 10 carbon atoms or a alkenylene group with 2 to 10 carbon atoms, which may optionally have functional groups, in particular OH-groups as substituents. Preferably, the group is a divalent alkyl group having from 2 to 4 carbon atoms. It is preferably a group selected from the group of methylene groups, 1,2-ethylene groups —$CH_2$—$CH_2$—, 1,2-propylene groups —$CH_2$—$CH(CH_3)$— or —$CH(CH_3)$—$CH_2$—, 1,3-propylene groups —$CH_2$—$CH_2$—$CH_2$— or 1,4-butylene groups.

Specific examples of surfactants of formula (I) include $C_{32}H_{65}O$—$BO_7$—$PO_7$—$EO_{25}$—$SO_3^-$ 1/b $M^{b+}$, $C_{32}H_{65}O$—$PO_7$-$EO_6$—$SO_3^-$ 1/b $M^{b+}$, $C_nH_{2n+1}O$-$EO_3$—$SO_3^-$ 1/b $M^{b+}$ with n=12 to 15, $C_nH_{2+1}O$-$EO_{12}$—$SO_3^-$ 1/b $M^{b+}$ with n=12 to 15, $C_nH_{2n+1}O$—$PO_7$—$SO_3^-$ 1/b $M^{b+}$ with n=16 to 178, $C_nH_{2n+1}O$—$PO_7$-$EO_5$—$SO_3^-$ 1/b $M^{b+}$ with n=16 to 17, $C_{13}H_{27}O$—$PO_7$—$SO_3^-$ 1/b $M^{b+}$, $C_{20}H_{41}O$—$PO_7$-$EO_{10}$—$SO_3^-$ 1/b $M^{b+}$. In yet another embodiment, the anionic ether surfactant has a formula $R^1O$—$BO_7$—$PO_7$-$EO_{25}$—$SO_3^-$ 1/b $M^{b+}$, wherein $R^1$ is a $C_{32}H_{65}$-group. Preferably, $M^{b+}$ is $Na^+$.

The surfactants of formula (I) may be synthesized using one or more Guerbet alcohol (GA) of the general formula $R^1$—OH as starting material. The term "Guerbet alcohol" is well known to those skilled in the art. Reference is made by way of example to "Alcohols, Aliphatic", page 10 in Ullmann's Encyclopedia of Industrial Chemistry, Seventh Edt., Electronic Release, 2008, Wiley-VCH, Weinheim, N.Y., and the literature cited there. In the course of the Guerbet reaction, primary alcohols are ultimately dimerized at high temperatures (like 230° C.) in the presence of suitable catalysts, in particular base catalysts to primary alcohols branched in 2-position. According to the literature, the primary products formed from the alcohols are aldehydes which subsequently dimerize to saturated alcohols by aldol condensation with elimination of water and subsequent hydrogenation. As well as the main product, different by-products can also form, for example unsaturated α-branched primary alcohols if the hydrogenation of the double bond does not proceed to completion, or more particularly branched primary alcohols which have additional branches in the side chain or main chain.

The following equation provides a typical example of the Guerbet reaction in which two molecules of a $C_{16}$-alcohol are dimerized yielding a $C_{32}$ alcohol branched in 2-position. As can be seen easily, the branching is in about mid-chain.

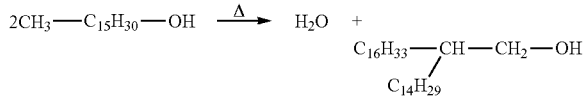

For a Guerbet alcohol having n carbon atoms the general formula is the following:

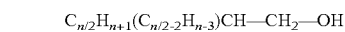

Generally speaking, in the Guerbet reaction one or more alcohols $R^2$—OH are used as starting material wherein $R^2$—OH is an aliphatic, preferably linear alcohol and wherein the average number of carbon atoms in $R^2$ is 6 to 18. The alcohol may be alternatively branched beginning with the 3-position. In case only one alcohol $R^2$—OH is used (which is preferred), the number of carbon atoms in the resulting Guerbet alcohol will necessarily be even, and the number of carbon atoms in $R^2$ will be n/2. If a mixture of two different alcohols is used, a mixture of different Guerbet alcohols will be obtained which may also have an odd number of carbon atoms.

Guerbet alcohols are branched and offer a way to achieve high molecular weight, highly and precisely branched alcohols (large hydrophobes) that can be transformed into surfactants. Phase behavior studies conducted by the present inventors have shown that such surfactants have exaggerated hydrophobicity and are capable of solubilizing higher amounts of crude oil. However, an inherent disadvantage of these GA derivatives is the high cost of the GA. This is mainly attributable to the high purity of the alcohol which necessitates the driving of the reaction to near completion.

In order to make these molecules cost competitive, in a preferred embodiment of invention the present inventors have made a lower cost Guerbet alcohol where in the Guerbet reaction is carried out to about 85 to less than 100% by weight yield leaving about up to 15% of "monomer" alcohol $R^2$—OH in the Guerbet alcohol product. Such yield may be obtained by applying less reaction time and/or less reaction temperature than required for 100% yield. Such a way to carry out the reaction requires less reactor time and therefore is less expensive. By the way of example, the yield may be 85%, 86%, 87%, 88%, 89%, 90%, 91%, 92%, 93%, 94%, 95%, 96%, 97%, 98% or 99%. The remaining alcohols $R^2$—OH are not separated and become converted to surfactants as the Guerbet alcohols $R^1$—OH. The inventors found that in general amounts of up to 15% of $R^2$—OH do not affect adversely the properties of the surfactants in course to enhanced oil recovery. The surfactant based on the Guerbet alcohol will provide high oil solubilization whereas surfactant based on the monomer alcohol $R^2$—OH will function as a hydrophilic cosurfactant assisting in the aqueous stability of the Guerbet surfactant. This minimizes the need for using cosolvents in the surfactant formulation.

Preferably, the Guerbet reaction is carried out at a temperature range of about 175° C. to 275° C., more preferably at a temperature range of about 220° C. to 250° C., and most preferred at around 230° C. Examples of reaction temperatures comprise 175° C., 190° C., 200° C., 220° C., 230° C., 240° C., 250° C., and 275° C.

The base used as catalyst for the Guerbet reaction preferably comprises NaOH or KOH.

The Guerbet alcohol $R^1$—OH which optionally comprises some $R^2$—OH is alkoxylated in the next process step. The procedure for alkoxylations is known in principle to the person skilled in the art. It is likewise known to those skilled in the art that the reaction conditions, especially the selection of the catalyst, can influence the molecular weight distribution of the alkoxylates.

The GA-alkoxylates can be prepared, for example, by base-catalyzed alkoxylation. To this end, the alcohol $R^1$—OH, which optionally comprises some $R^2$—OH can be admixed in a pressure reactor with alkali metal hydroxides, preferably potassium hydroxide or with alkali metal alkoxides, for example sodium methoxide. By means of reduced pressure (for example <100 mbar) and/or an increase in the temperature (from 30 to 150° C.), it is possible to draw off water still present in the mixture. The alcohol is then present as the corresponding alkoxide. This is followed by inertization with inert gas (e.g. nitrogen) and addition of the alkylene oxide(s) stepwise at temperatures of from 60 to 180° C. up to a pressure of max. 10 bar. At the end of the reaction, the catalyst can be neutralized by adding acid (e.g. acetic acid or phosphoric acid) and can be filtered off if required.

In another embodiment, the Guerbet alcohol alkoxylates may be synthesized by means of techniques known to those skilled in the art which lead to narrower molecular weight distributions than in the case of base-catalyzed synthesis. To this end, the catalysts used may, for example, be double hydroxide clays, as described in DE 43 25 237 A1. The alkoxylation can more preferably be effected using double metal cyanide catalysts (DMC catalysts). Suitable DMC catalysts are disclosed, for example, in DE 102 43 361 A1, especially paragraphs [0029] to and the literature cited therein. For example, catalysts of the Zn—Co type can be used. To perform the reaction, alcohol $R^1$—OH, which optionally comprises some $R^2$—OH can be admixed with the catalyst, and the mixture dewatered as described above and reacted with the alkylene oxides as described. Typically, not more than 250 ppm of catalyst based on the mixture is used, and the catalyst can remain in the product owing to this small amount. Inventive surfactants prepared by means of DMC catalysis are notable in that they result in a better lowering of the interfacial tension in the water-mineral oil system than products prepared by means of KOH catalysis.

The GA-alkoxylates (A) can additionally also be prepared by acid-catalyzed alkoxylation. The acids may be Bronsted or Lewis acids. To perform the reaction, alcohol $R^1$—OH, which optionally comprises some $R^2$—OH can be admixed with the catalyst, and the mixture can be dewatered as described above and reacted with the alkylene oxides as described. At the end of the reaction, the catalyst can be neutralized by adding a base, for example KOH or NaOH, and be filtered off if required.

The block structure indicated in formula (I) is obtained by subsequently adding butylene oxide, propylene oxide, and ethylene oxide in the respective amounts necessary. In the preferred embodiment, the GA is butoxylated with x butylene oxide (BO) units to form a butoxylated GA, and then alkoxylated with y propylene oxide (PO) units and then z ethylene oxide (EO) units or both. The properties of the resultant surfactants may be tailored to fit EOR needs by the skilled artisan by selecting the number of BO, PO, and EO groups. The alkoxylated Guerbet alcohol comprises a terminal OH-group.

After the alkoxylation, the terminal OH-group of the alkoxylated GA obtained by the procedure disclosed is converted to the terminal group —X—$Y^{a-}$ a/b $M^{b+}$. Suitable procedures are well known to the skilled artisan.

Sulfation of a hydrophobe is the simplest and most versatile method of making anionic surfactants. The conversion to the sulfate can be effected, for example, by adding the OH group of the alkoxylate onto sulfur trioxide, chloro sulfuric acid, sulfamic acid or sulfuric acid and then neutralizing with, for example, sodium hydroxide solution. This can be carried out, for example, in a falling-film reactor. In this case, the terminal OH-group reacts with sulfur trioxide, chloro sulfuric acid or sulfuric acid and X consequently is a single bond.

Sulfonates are not as easily available as sulfates, however sulfonates have a better long term stability at higher temperatures, in particular at temperatures above about 65° C. to 70° C. The conversion to the sulfonates can be effected, for example, by substituting the OH group of the alkoxylate for Cl using phosgene or thionyl chloride. The reaction can be undertaken in the presence of a solvent, for example chlorobenzene. HCl released and $CO_2$ or $SO_2$ released can advantageously be removed from the system by stripping with nitrogen, such that ether cleavage is suppressed. The alkyl alkoxychlorine compound is then reacted with an aqueous solution of sodium sulfite, which substitutes the chloride for sulfite to obtain the alkyl ether sulfonate. The substitution can be undertaken in the presence of a phase mediator (for example $C_1$- to $C_8$-alcohols) at a temperature of 100-180° C. and pressure. Alternatively, sulfonates may be obtained by adding vinylsulfonic acid onto the Guerbet alcohol alkoxylate. Details on this subject are described, for example, in EP 311 961 A1. In another alternative, the alkyl alkoxylates may be reacted with sultones, for example 1,3-propanesultone or 1,4-butanesultone yielding products with a terminal —$CH_2$—$CH_2$—$CH_2$—$SO_3M$ group (i.e. X=—$CH_2$—$CH_2$—$CH_2$—) or a terminal —$CH_2$—$CH_2$—$CH_2$—$CH_2$—$SO_3M$ group. GA ether sulfonates with a terminal —$CH_2$—CH(OH)—$CH_2$—$SO_3M$ group (i.e. X=—$CH_2$—CH(OH)—$CH_2$—) are obtainable by the reaction of the GA alkoxylate with epichlorohydrin and subsequent nucleophilic substitution of the chloride group for sodium sulfite.

Terminal carboxylate groups —COOM may be obtained by oxidation. Suitable oxidizing agents for this purpose are in principle all oxidizing agents, if appropriate in conjunction with suitable catalysts which can oxidize the terminal OH group of the alkyl alkoxylate to the —COOM group without oxidizing other parts of the molecule to a high degree. The oxidation can be undertaken, for example, with the aid of air or oxygen using a noble metal catalyst (for example a catalyst based on palladium). In a further embodiment of the invention, the GA ether carboxylates can also be prepared by adding (meth)acrylic acid or a (meth)acrylic ester onto the GA alkyl alkoxylate by means of a Michael addition. If the esters are used, they are hydrolyzed after the addition. These synthesis variants afford—according to whether acrylic acid or (meth)acrylic acid or esters thereof have been used—terminal —$CH_2$—$CH_2$—COOM or —$CH_2$—CH($CH_3$)—COOM groups.

Phosphate groups may be obtained by esterification with phosphoric acid or phosphorous pentachloride and phosphonates may be obtained by reaction of the GA ether alkoxylate with vinyl phosphonic acid.

The present invention can be used in any application (e.g., surface or near-surface treatments, downhole or for Enhanced Oil Recovery) that involves high temperature conditions, such as, environmental clean up of ground water contaminated by oils and other organic solvents.

One further embodiment of the present invention describes a composition for enhanced oil recovery (EOR), environmental ground water cleanup, and other surfactant based operations, preferably enhanced oil recovery comprising at least one or more surfactants and a solvent, wherein at least one or more of the surfactants have a general formula (I)

$$R^1O—BO_x—PO_y—EO_z—X—Y^{a-} a/b M^{b+} \qquad (I),$$

wherein $R^1$, X, Y, M, n, x, y, z, a, b have the meaning as defined above.

Preferably, the one or more surfactants of formula (I) are selected from the group consisting of $C_{32}H_{65}O-BO_7-PO_7-EO_{25}-SO_3^- \ 1/b \ M^{b+}$, $C_nH_{2n+1}O-EO_3-SO_3^- \ 1/b \ M^{b+}$ with n=12 to 15, $C_nH_{2n+1}O-EO_{12}-SO_3^- \ 1/b \ M^{b+}$ with n=12 to 15, $C_nH_{2n+1}O-PO_7-SO_3^- \ 1/b \ M^{b+}$ with n=16 to 18, $C_nH_{2n+1}O-PO_7-EO_5-SO_3^- \ 1/b \ M^{b+}$ with n=16 to 17, $C_{13}H_{27}O-PO_7-SO_3^- \ 1/b \ M^{b+}$, $C_{20}H_{41}O-PO_7-EO_{10}-SO_3^- \ 1/b \ M^{b+}$.

Preferably, the solvent comprises water, hard brine, hard water, or any combinations thereof. In addition to water, the compositions can optionally also comprise organic solvents miscible with water or at least dispersible in water. Such additions serve in particular for stabilizing the surfactant solution during the storage or the transport to the oil field. However, the amount of such additional solvents should as a rule not exceed 50% by weight, preferably 20% by weight and particularly preferably 10% by weight. In a particularly advantageous embodiment of the invention, exclusively water is used for formulation. Examples of solvents miscible with water comprise in particular alcohols, such as methanol, ethanol or propanol.

The composition mentioned above furthermore comprises one or more alkalinity generating agents, and a solvent, wherein the one or more anionic ether sulfate surfactants, the one or more alkalinity generating agents are dissolved in the solvent. Preferably, the one or more alkalinity generating agents comprise alkali earth metal hydroxides, NaOH, KOH, LiOH, ammonia, $Na_2CO_3$, $NaHCO_3$, Na-metaborate, sodium silicate, sodium orthosilicate, $EDTANa_4$, other polycarboxylates or any combinations thereof.

The composition of the present invention is used alone or in an alkaline-surfactant-polymer formulation for EOR applications and contains 0.01% to 1.5% by weight of the one or more alkalinity generating agents. Examples of concentrations comprise 0.1%, 0.15%, 0.2%, 0.25% 0.3%, 0.35%, 0.4%, 0.45%, 0.5%, and so on of the one or more alkalinity generating agents.

In another embodiment, the composition may additionally comprise cosurfactants selected from sulfate, sulfonate, carboxylate anion based surfactants, ether sulfates, ethoxy sulfates, propoxy sulfates, perfluorooctanoate (PFOA or PFO), perfluorooctanesulfonate (PFOS), sodium dodecyl sulfate (SDS), ammonium lauryl sulfate, alkyl sulfate salts, sodium lauryl ether sulfate (SLES), alkyl benzene sulfonate, soaps, fatty acid salts, alkyl polyglucosides, cationic surfactants or betanic surfactants.

In yet another embodiment, the composition may comprises oligomeric or polymeric surfactants. With such polymeric cosurfactants, the amount of surfactant which is required for the formation of a microemulsion can advantageously be reduced. Such polymeric cosurfactants are therefore also referred to as "microemulsion boosters". Examples of such polymeric surfactants comprise amphiphilic block copolymers which comprise at least one hydrophilic and at least one hydrophobic block. Examples comprise polypropylene oxide-polyethylene oxide block copolymers, polyisobutene-polyethylene oxide block copolymers and comb polymers having polyethylene oxide side chains and a hydrophobic main chain, the main chain preferably comprising substantially olefins or (meth)acrylates as structural units. The term "polyethylene oxide" is intended here in each case to include polyethylene oxide blocks according to the above definition which comprise propylene oxide units. Further details of such surfactants are disclosed in WO 2006/131541.

Another embodiment of the present invention discloses a method of enhanced oil recovery from a hydrocarbon bearing formation. In the method a suitable composition comprising at least a solvent and an anionic ether surfactant having a general formula (I)

$$R^1O-BO_x-PO_y-EO_z-X-Y^{a-}a/bM^{b+} \qquad (I),$$

wherein $R^1$, X, Y, M, n, x, y, z, a, b have the meaning as defined above is injected into the hydrocarbon bearing formation through at least one injection well and crude oil is removed from the deposit through at least one production well.

In this context, the term "crude oil" does not of course mean single-phase oil but means the customary crude oil-water emulsions. As a rule, a deposit is provided with a plurality of injection wells and with a plurality of production wells.

After the forcing in of the surfactant formulation, the so-called "surfactant flooding", water ("water flooding") or preferably a more highly viscous, aqueous solution of a polymer having a pronounced thickening effect ("polymer flooding") can be injected into the formation for maintaining the pressure. However, other known techniques are those in which the surfactants are first allowed to act on the formation. A further known technique is the injection of the solution comprising surfactant and polymer having a thickening effect, followed by a solution of polymer having a thickening effect. Details of the technical procedure of "surfactant flooding", "water flooding" and "polymer flooding" are known to a person skilled in the art and he uses a corresponding technique according to the type of deposit.

In a preferred embodiment of the invention the abovementioned composition for enhanced oil recovery (EOR) may be used. Also preferably, an alkaline-surfactant-polymer formulation (ASP) may be used.

The deposits in which the process is used have as a rule a temperature of at least 15° C., for example from 15 to 130° C., preferably a temperature of at least 25° C. and particularly preferably at least 30° C., for example from 30 to 120° C.

The total concentration of all surfactants together is preferably from 0.05 to 5% by weight, based on the total amount of the aqueous surfactant formulation, more preferably from 0.1 to 2.5% by weight. The person skilled in the art makes a suitable choice according to the desired properties, in particular according to the conditions in the mineral oil formation. It is clear here to a person skilled in the art that the concentration of the surfactants may change after injection into the formulation because the formulation can mix with formation water or surfactants can also be absorbed on solid surfaces of the formation. It is the major advantage of the mixtures used according to the invention that the formation of a microemulsion is not excessively influenced by such a change in the total concentration.

If cosurfactants are present besides the surfactants of formula (I) the amount of surfactants of formula (I) in general should be at least 10% by weight relating to the amount of all surfactants present, preferably at least 20% and more preferably at least 50%.

It is of course possible and as a rule also advisable first to prepare a concentrate which is diluted only on site to the desired concentration for injection into the formation. As a rule, the total concentration of the surfactants in such a concentrate is from 10 to 45% by weight.

The surfactants according to the invention reduce the interfacial tension between water and oil and therefore improve the mobility of oil in the formation. In a preferred embodiment of the invention, the interfacial tension should be reduced at least to less than 0.1 mN/m, more preferably it should be reduced to at least 0.01 mN/m. Preferably, the surfactants may be used for "Winsor Type III micro emulsion flooding".

Referring to FIG. 1, an exemplary offshore oil platform is schematically illustrated and generally designated 10. Semi-submersible platform 12 is centered over submerged hydrocarbon-bearing formation 14 located below sea floor 16. Subsea conduit 18 extends from deck 20 of platform 12 to wellhead installation 22 including blowout preventers 24. Platform 12 is shown with hoisting apparatus 26 and derrick 28 for raising and lowering pipe strings such as work string 30.

Wellbore 32 extends through the various earth strata including hydrocarbon-bearing formation 14. Casing 34 is cemented within wellbore 32 by cement 36. Work string 30 may include various tools including, for example, sand control screen assembly 38 which is positioned within wellbore 32 adjacent to hydrocarbon-bearing formation 14. Also extending from platform 12 through wellbore 32 is fluid delivery tube 40 having fluid or gas discharge section 42 positioned adjacent to hydrocarbon-bearing formation 14, shown with production zone 48 between packers 44, 46. When it is desired to treat the near-wellbore region of hydrocarbon-bearing formation 14 adjacent to production zone 48, work string 30 and fluid delivery tube 40 are lowered through casing 34 until sand control screen assembly 38 and fluid discharge section 42 are positioned adjacent to the near-wellbore region of hydrocarbon-bearing formation 14 including perforations 50. Thereafter, a composition described herein is pumped down delivery tube 40 to progressively treat the near-wellbore region of hydrocarbon-bearing formation 14.

Surfactant Synthesis

General Procedure 1: Alkoxylation using KOH as catalyst: In a 2 liter autoclave the Guerbet alcohol (1.0 eq) chosen is mixed with aqueous KOH-solution, which contains 50% KOH by weight. Amount of KOH is 0.3 weight % of desired product. Under stirring mixture is heated at 100° C. and 20 mbar for 2 h and water is removed. After flushing 3 times with $N_2$, nitrogen is added until pressure of 1.3 bar is reached and temperature is raised to 120-130° C. The Alkylene oxides are added consecutively in such a manner that temperature remains at 125° C.-135° C. (in case of ethylene oxide) or 130-140° C. (in case of propylene oxide) or 135-145° C. (in case of butylene oxide). After 5 h stirring at 125-145° C., reactor is flushed with $N_2$ and cooled down to 70° C. in order to take material out of the reactor. The basic reaction mixture is neutralized with acetic acid or commercial available magnesium-silicates, which will be filtered off afterwards. The product is characterized using 1H-NMR-spektra in $CDCl_3$, a size-exclusion-chromatography, and a determination of the OH-number. The yield obtained is notified.

General Procedure 2: Sulfation using chloro sulfonic acid: In a 1 liter round bottom flask the alkyl alkoxylate (1.0 eq) to be sulfated is diluted with dichloromethane (150 weight % of alkylalkoxylate) and cooled down to 5-10° C. Chloro sulfonic acid (1.1 eq) is added in such a way, that temperature does not increase beyond 10° C. Afterwards reaction mixture is allowed to warm up to room temperature and is stirred 4 h at this temperature under constant $N_2$ gas flow. This reaction mixture is added drop wise to an aqueous NaOH-solution of half volume in such a way, that temperature is kept below 15° C. Amount of sodium hydroxide is calculated in such a way, that a slight excess regarding the used Chloro sulfonic acid results. Resulting pH-value is 9-10. Dichloromethane is removed under vacuum in a rotary evaporator at temperature below 50° C. The final product is characterized using 1H-NMR-spektra and water content of solution will be determined (ca. 70%). Alternatively, the sulfation of the alkoxylate can be carried out using 1.1 equivalents of Sulfamic acid at 75-85° C.

Synthesized surfactants: For the examples and comparative examples a commercially available $C_{32}$-Guerbet alcohol (2-Tetradecyloctadecan-1-ol; $C_{16}H_{33}$—$CH(C_{14}H_{29})$—$CH_2OH$; >98% by weight purity) was used. With the above-mentioned general procedures, the surfactants summarized in Table 1 were synthesized.

TABLE 1

Surfactants synthesized using the general procedures.

| | |
|---|---|
| Example 1 | $C_{32}H_{65}O$—$(BO)_7$—$(PO)_7$—$SO_3Na$ |
| Example 2 | $C_{32}H_{65}O$—$(BO)_7$—$(PO)_7$—$(EO)_{25}$—$SO_3Na$ |
| Comparative example 1 | $C_{32}H_{65}O$—$(PO)_7$—$(EO)_{10}$—$SO_3Na$ |
| Comparative example 2 | $C_{32}H_{65}O$—$(BO)$—$(PO)_7$—$(EO)_{10}$—$SO_3Na$ |
| Comparative example 3 | $C_{32}H_{65}O$—$(PO)_7$—$(BO)_7$—$SO_3Na$ |

Example 1 provides a surfactant according to the present invention. The comparative examples provide surfactants which are not within the scope of the present invention. The surfactant of Comparative example 1 has no poly butoxy block, that of comparative example 2 comprises only one butoxy unit, and in comparative example 3, the polybutoxy block and the polypropoxy block are arranged in the reverse order.

Application Tests—Test Series 1

SP* and interfacial tension, description of the test procedure a) General principle: Interfacial tension between oil and water is measured by solubilization parameter SP*, which is an accepted method within scientific community to determine an approximate value of interfacial tension. Solubilization parameter SP* is amount of solubilized ml of oil per ml used surfactant in a balanced microemulsion of Windsor Type III. A balanced microemulsion contains similar amounts of water and oil. In such a case interfacial tension σ (IFT) can be calculated using equation $IFT \approx 0.3/(SP^*)^2$ (C. Huh, J. Coll. Interf. Sc., Vol. 71, No. 2 (1979)).

b) Procedure: For determination of SP* a 100 ml graduated cylinder with stirring bar is filled with 20 ml oil and 20 ml saline water. Surfactants in certain concentrations are added afterwards. Temperature is increased stepwise from 20 to 90° C. and temperature window is notified when a microemulsion Winsor type III is formed. A 3-phase system is formed: upper phase is oil, middle phase microemulsion, lower phase water. If upper and lower phase are equal and do not change over 12 h optimum temperature ($T_{opt}$) is reached. Volume of middle phase is determined, from which surfactant volume is subtracted. Resulting value is divided by two. This volume is divided by volume of added surfactant. Result is notified as SP*. Used oil is a model oil like decane or the real crude oil. Used water contains NaCl or is the original water from the reservoir.

Test results: A 1:1 mixture out of decane and a NaCl-solution is mixed with butyl diethylene glycol (BDG). BDG acts as co-solvent and is not incorporated in calculation of SP*. The surfactant composition comprises 3 parts by weight of the Guerbet alkoxy sulfate according to example 1 and comparative examples 1 to 3 respectively and 1 part by weight of sodium-dodecene benzene sulfonate as cosurfactant. The total concentration is given in weight % with respect to all components of the composition. The results are presented in Table 2.

As demonstrated in Table 2 the $C_{32}$-Guerbet based surfactant of example 1, i.e. the surfactant $C_{32}H_{65}$—(BO)$_7$—(PO)$_7$—OSO$_3$Na yields in an ultralow interfacial tension against decane of $4 \times 10^{-5}$ mN/m. In contrast, surfactants comprising no poly butoxy block or only one butoxy unit and surfactants in which the polybutoxy block is not directly bound to the Guerbet alcohol unit, the IFT values are significantly higher. Interestingly, the incorporation of one butoxy unit was not very effective in reducing the interfacial tension further.

Application Tests—Test Series 2
Phase Behavior Procedures

Phase Behavior Screening: Phase behavior studies have been used to characterize chemicals for EOR. There are many benefits in using phase behavior as a screening method. Phase Behavior studies are used to determine: (1) the effect of electrolytes; (2) oil solubilization, IFT reduction, (3) microemulsion densities; (4) surfactant and microemulsion viscosities; (5) coalescence times; (6) identify optimal surfactant-cosolvent formulations; and/or (7) identify optimal formulation for coreflood studies.

Thermodynamically stable phase can form with oil, water and surfactant mixtures. Surfactants form micellar structures at concentrations above the critical micelle concentration (CMC). The emulsion coalesces into a separate phase at the oil-water interface and is referred to as a microemulsion. A microemulsion is a surfactant-rich distinct phase consisting of surfactant, oil and water and possibly co-solvents and other components. This phase is thermodynamically stable in the sense that it will return to the same phase volume at a given temperature. Some workers in the past have added additional requirements, but for the purposes of this engineering study, the only requirement will be that the microemulsion is a thermodynamically stable phase.

electrolyte concentration where the optimum solubilization ratio occurs is referred to as the Optimal Salinity (S*).

Determining Interfacial Tension: Efficient use of time and lab resources can lead to valuable results when conducting phase behavior scans. A correlation between oil and water solubilization ratios and interfacial tension was suggested by Healy and Reed (1976) and a theoretical relationship was later derived by Chun Huh (1979). Lowest oil-water IFT occurs at optimum solubilization as shown by the Chun Huh theory. This is equated to an interfacial tension through the Chun Huh equation, where IFT varies with the inverse square of the solubilization ratio:

$$\gamma = \frac{C}{\sigma^2} \qquad (1)$$

For most crude oils and microemulsions, C=0.3 is a good approximation. Therefore, a quick and convenient way to estimate IFT is to measure phase behavior and use the Chun-Huh equation to calculate IFT. The IFT between microemulsions and water and/or oil can be very difficult and time consuming to measure and is subject to larger errors, so using the phase behavior approach to screen hundreds of combinations of surfactants, co-surfactants, co-solvents, electrolytes, oil, and so forth is not only simpler and faster, but avoids the measurement problems and errors associated with measuring IFT especially of combinations that show complex behavior (gels and so forth) and will be screened out anyway. Once a good formulation has been identified, then it is still a good idea to measure IFT.

Equipment: Phase behavior studies are created with the following materials and equipment.

TABLE 2

Results of the application tests.

| No. | Surfactant | Total surfactant conc. [%] | BDG [%] | NaCl [%] | $T_{opt}$ [° C.] | SP* | IFT [mN/m] |
|---|---|---|---|---|---|---|---|
| 1 | $C_{32}H_{65}O$—(BO)$_7$—(PO)$_7$—SO$_3$Na + $C_{12}H_{25}$—$C_6H_4SO_3Na$ (3:1) | 0.4 | 2 | 1.6 | 71.5 | 85 | 0.00004 |
| C1 | $C_{32}H_{65}O$—(PO)$_7$—(EO)$_{10}$—SO$_3$Na + $C_{12}H_{25}$—$C_6H_4SO_3Na$ (3:1) | 0.4 | 2 | 4.8 | 72 | 37 | 0.00022 |
| C2 | $C_{32}H_{65}O$—(BO)—(PO)$_7$—(EO)$_{10}$—SO$_3$Na + $C_{12}H_{25}$—$C_6H_4SO_3Na$ (3:1) | 0.4 | 2 | 5 | 74 | 25 | 0.00048 |
| C3 | $C_{32}H_{65}O$—(PO)$_7$—(BO)$_7$—SO$_3$Na + $C_{12}H_{25}$—$C_6H_4SO_3Na$ (3:1) | 0.4 | 2 | 1.3 | 70 | 31 | 0.00031 |

The phase transition is examined by keeping all variables fixed except for the scanning variable. The scan variable is changed over a series of pipettes and may include, but is not limited to, salinity, temperature, chemical (surfactant, alcohol, electrolyte), oil, which is sometimes characterized by its equivalent alkane carbon number (EACN), and surfactant structure, which is sometimes characterized by its hydrophilic-lipophilic balance (HLB). The phase transition was first characterized by Winsor (1954) into three regions: Type I—excess oleic phase, Type III—aqueous, microemulsion and oleic phases, and the Type II—excess aqueous phase. The phase transition boundaries and some common terminology are described as follows: Type I to III—lower critical salinity, Type III to II—upper critical salinity, oil solubilization ratio (Vo/Vs), water solubilization ratio (Vw/Vs), the solubilization value where the oil and water solubilization ratios are equal is called the Optimum Solubilization Ratio (a*), and the Mass Balance: Mass balances are used to measure chemicals for mixtures and determine initial saturation values of cores.

Water Deionizer: Deionized (DI) water is prepared for use with all the experimental solutions using a Nanopure™ filter system. This filter uses a recirculation pump and monitors the water resistivity to indicate when the ions have been removed. Water is passed through a 0.45 micron filter to eliminate undesired particles and microorganisms prior to use.

Borosilicate Pipettes: Standard 5 mL borosilicate pipettes with 0.1 mL markings are used to create phase behavior scans as well as run dilution studies with aqueous solutions. Ends are sealed using a propane and oxygen flame.

Pipette Repeater: An Eppendorf Repeater Plus® instrument is used for most of the pipetting. This is a handheld dispenser calibrated to deliver between 25 microliter and 1 ml increments. Disposable tips are used to avoid contamination between stocks and allow for ease of operation and consistency.

Propane-oxygen Torch: A mixture of propane and oxygen gas is directed through a Bernz-O-Matic flame nozzle to create a hot flame about ½ inch long. This torch is used to flame-seal the glass pipettes used in phase behavior studies.

Convection Ovens: Several convection ovens are used to incubate the phase behaviors and core flood studies at the reservoir temperatures. The phase behavior pipettes are primarily kept in Blue M and Memmert ovens that are monitored with mercury thermometers and oven temperature gauges to ensure temperature fluctuations are kept at a minimal between recordings. A large custom built flow oven was used to house most of the core flood studies and enabled fluid injection and collection to be done at reservoir temperature.

pH Meter: An ORION research model 701/digital ion analyzer with a pH electrode is used to measure the pH of most aqueous samples to obtain more accurate readings. This is calibrated with 4.0, 7.0 and 10.0 pH solutions. For rough measurements of pH, indicator papers are used with several drops of the sampled fluid.

Phase Behavior Calculations: The oil and water solubilization ratios are calculated from interface measurements taken from phase behavior pipettes. These interfaces are recorded over time as the mixtures approached equilibrium and the volume of any macroemulsions that initially formed decreased or disappeared. The procedure for creating phase behavior studies will be discussed later.

Oil Solubilization Ratio: The oil solubilization ratio is defined as the volume of oil solubilized divided by the volume of surfactant in microemulsion. All the surfactant is presumed to be in the emulsion phase. The oil solubilization ratio is applied for Winsor type I and type III behavior. The volume of oil solubilized is found by reading the change between initial aqueous level and excess oil (top) interface level. The oil solubilization parameter is calculated as follows:

$$\sigma_o = \frac{V_o}{V_s} \qquad (2)$$

$\sigma_o$=oil solubilization ratio
$V_o$=volume of oil solubilized
$V_s$=volume of surfactant Water Solubilization Ratio: The water solubilization ratio is defined as the volume of water solubilized divided by the volume of surfactant in microemulsion. All the surfactant is presumed to be in the emulsion phase. The water solubilization ratio is applied for Winsor type III and type II behavior. The volume of water solubilized is found by reading the change between initial aqueous level and excess water (bottom) interface level. The water solubilization parameter is calculated as follows:

$$\sigma_w = \frac{V_w}{V_s} \qquad (3)$$

$\sigma_w$=water solubilization ratio
$V_w$=volume of water solubilized

Optimum Solubilization Ratio: The optimum solubilization ratio occurs where the oil and water solubilization is equal. The coarse nature of phase behavior screening often does not include a data point at optimum, so the solubilization curves are drawn for the oil and water solubilization and the intersection of these two curves is defined as the optimum. The following is true for the optimum solubilization ratio:

$$\sigma_o = \sigma_w = \sigma^* \qquad (4)$$

$\sigma^*$=optimum solubilization parameter

Phase Behavior Methodology: The methods for creating, measuring and recording observations are described in this section. Scans are made using a variety of electrolyte mixtures described below. Oil is added to most aqueous surfactant solutions to see if a microemulsion formed, how long it took to form and equilibrate if it formed, what type of microemulsion formed and some of its properties such as viscosity. However, the behavior of aqueous mixtures without oil added is also important and is also done in some cases to determine if the aqueous solution is clear and stable over time, becomes cloudy or separated into more than one phase.

Preparation of Samples: Phase Behavior Samples are Made by First Preparing Surfactant stock solutions and combining them with brine stock solutions in order to observe the behavior of the mixtures over a range of salinities. All the studies are created at or above 0.1 wt % active surfactant concentration, which is above the typical CMC of the surfactant.

Solution Preparation: Surfactant stocks are based on active weight-percent surfactant (and co-surfactant when incorporated). The masses of surfactant, co-surfactant, co-solvent and de-ionized water (DI) are measured out on a balance and mixed in glass jars using magnetic stir bars. The order of addition is recorded on a mixing sheet along with actual masses added and the pH of the final solution. Brine solutions are created at the necessary weight percent concentrations for making the scans.

Surfactant Stock: The chemicals being tested are first mixed in a concentrated stock solution that usually consisted of a primary surfactant, co-solvent and/or co-surfactant along with de-ionized water. The quantity of chemical added is calculated based on activity and measured by weight percent of total solution. Initial studies are at about 1-3% active surfactant so that the volume of the middle microemulsion phase would be large enough for accurate measurements assuming a solubilization ratio of at least 10 at optimum salinity.

Polymer Stock: Often these stocks were quite viscous and made pipetting difficult so they are diluted with de-ionized water accordingly to improve ease of handling. Mixtures with polymer are made only for those surfactant formulations that showed good behavior and merited additional study for possible testing in core floods. Consequently, scans including polymer are limited since they are done only as a final evaluation of compatibility with the surfactant.

Pipetting Procedure: Phase behavior components are added volumetrically into 5 ml pipettes using an Eppendorf Repeater Plus or similar pipetting instrument. Surfactant and brine stocks are mixed with DI water into labeled pipettes and brought to temperature before agitation. Almost all of the phase behavior studies are initially created with a water oil ratio (WOR) of 1:1, which involved mixing 2 ml of the aqueous phase with 2 ml of the evaluated crude oil or hydrocarbon, and different WOR studies are mixed accordingly. The typical phase behavior scan consisted of 10-20 pipettes, each pipette being recognized as a data point in the series.

Order of Addition: Consideration had to be given to the addition of the components since the concentrations are often several fold greater than the final concentration. Therefore, an order is established to prevent any adverse effects resulting from surfactant or polymer coming into direct contact with the concentrated electrolytes. The desired sample compositions are made by combining the stocks in the following order: (1) Electrolyte stock(s); (2) De-ionized water; (3) Surfactant stock; (4) Polymer stock; and (5) Crude oil or hydrocarbon. Any air bubbles trapped in the bottom of the pipettes are tapped out (prior to the addition of surfactant to avoid bubbles from forming).

Initial Observations: Once the components are added to the pipettes, sufficient time is allotted to allow all the fluid to drain down the sides. Then aqueous fluid levels are recorded before the addition of oil. These measurements are marked on record sheets. Levels and interfaces are recorded on these documents with comments over several days and additional sheets are printed as necessary.

Sealing and Mixing: The pipettes are blanketed with argon gas to prevent the ignition of any volatile gas present by the flame sealing procedure. The tubes are then sealed with the propane-oxygen torch to prevent loss of additional volatiles when placed in the oven. Pipettes are arranged on the racks to coincide with the change in the scan variable. Once the phase behavior scan is given sufficient time to reach reservoir temperature (15-30 minutes), the pipettes are inverted several times provide adequate mixing. Tubes are observed for low tension upon mixing by looking at droplet size and how uniform the mixture appeared. Then the solutions are allowed to equilibrate over time and interface levels are recorded to determine equilibration time and surfactant performance.

Measurements and Observations: Phase behavior studies are allowed to equilibrate in oven that is set to the reservoir temperature for the crude oil being tested. The fluid levels in the pipettes are recorded periodically and the trend in the phase behavior observed over time. Equilibrium behavior is assumed when fluid levels ceased to change within the margin of error for reading the samples.

Fluid Interfaces: The fluid interfaces are the most crucial element of phase behavior studies. From them, the phase volumes are determined and the solubilization ratios are calculated. The top and bottom interfaces are recorded as the scan transitioned from an oil-in-water microemulsion to a water-in-oil microemulsion. Initial readings are taken one day after initial agitation and sometimes within hours of agitation if coalescence appeared to happen rapidly. Measurements are taken thereafter at increasing time intervals (for example, one day, four days, one week, two weeks, one month and so on) until equilibrium is reached or the experiment is deemed unessential or uninteresting for continued observation.

The present inventors conducted studies to show the enhanced performance of Guerbet-BO—PO-EO sulfates surfactants in comparison to the surfactants with just PO-EO groups. The study was done by comparing the performances of the each component of the formulation by varying the concentrations.

The inventors formulated two system: (i) a BO derivative along with any other surfactants in equal proportion and (ii) another formulation with the same system but with a higher concentration of the surfactant with BO group in it. The solubilization plots for the two systems are shown in FIGS. 2A and 2B.

Figure 2A:
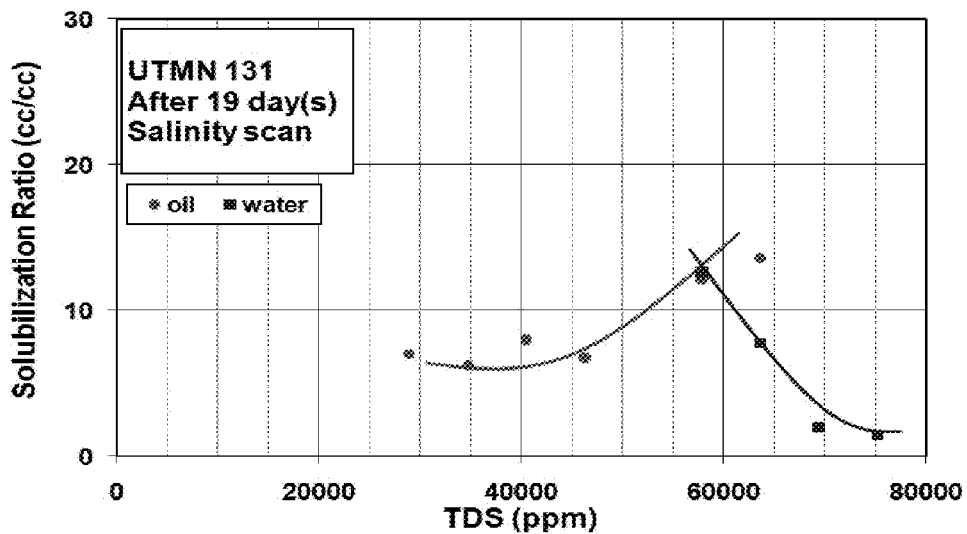
FIG. 2A is a solubilization plot for the system UTMN-131 comprising (all amounts % by weight), 0.33% $C_{32}H_{65}O$—$PO_7$-$EO_{10}$—$SO_3^-$ $Na^+$, 0.33% C15-18 Internal olefin sulfonate (IOS), (0.33% $C_{32}H_{65}O$—$BO_7$—$PO_7$-$EO_{25}$—$SO_3^-$ $Na^+$, 5% triethylene glycole monobutyl ether (TEGBE), 3.75% $EDTANa_4$ at 100° C.

Surfactant composition for the studies shown in FIG. 2A: 0.33% $C_{32}$-7PO-10EO-$SO_4$, 0.33% $C_{15}$-18 IOS, 0.33% $C_{32}$-7BO-7PO-25EO-$SO_4$, 0.5% TEGBE, 3.75% EDTA $Na_4$.

Figure 2B:
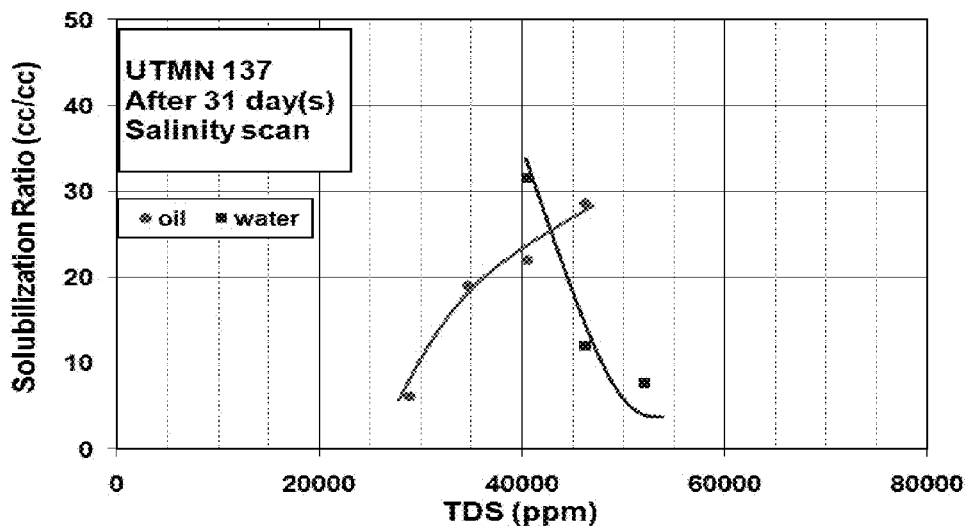
FIG. 2B is a solubilization plot for the system UTMN-137 comprising, comprising (all amounts % by weight), 0.33% $C_{32}H_{65}O$—$PO_7$-$EO_{10}$—$SO_3^-$ $Na^+$, 0.33% C15-18 Internal olefin sulfonate (IOS), 0.58% $C_{32}H_{65}O$—$BO_7$—$PO_7$-$EO_{25}$—$SO_3^-$ $Na^+$, 0.5% triethylene glycole monobutyl ether (TEGBE), 3.75% $EDTANa_4$ at 100° C.

Surfactant composition for the studies shown in FIG. 2B: 0.33% $C_{32}$-7PO-10EO-$SO_4$, 0.33% $C_{15}$-18 IOS, 0.58% $C_{32}$-7BO-7PO-25EO-$SO_4$, 0.5% TEGBE, 3.75% EDTA $Na_4$.

The composition of the brine used is presented in Table 3.

TABLE 3

Injection brine composition used in the phase behavior studies.

| | Injection Water (ppm) |
|---|---|
| Na | 18,300 |
| Ca | 650 |
| Mg | 2,110 |
| K | n/a |
| SO4 | 4,290 |
| Cl | 32,200 |
| CO3 | 0 |
| HCO3 | 120 |
| TDS | 57,670 |

Tables 4A and 4B shows phase behavior data recording sheets corresponding to plots shown in FIGS. 2A and 2B respectively. As seen from the plots the optimum solubilization ratio for the case 1 is around 11. The total surfactant concentration in that case is 1% (ref FIG. 2A). The formulation in the second case is exactly the same but with 25% more $C_{32}H_{65}O$—$(BO)_7$—$(PO)_7$-$(EO)_{25}$—$SO_3Na$ and so the total surfactant concentration is 1.25%. Theoretically with the increase in total surfactant concentration of the same formulation should yield the same solubilization ratio as it is given by (previously described in equation 2)

$$\sigma = V_o/V_s (cc/cc)$$

With the increase in total surfactant concentration the volume of oil solubilized also increases proportionally and eventually the solubilization ratio stays the same. So if just the total surfactant concentration of the system UTMN-131 was changed from 1% to 1.25% with all 3 components increased proportionally, there should be no change in the solubilization ratio. But it is seen that the 25% increase in $C_{32}H_{65}O$—$(BO)_7$—$(PO)_7$-$(EO)_{25}$—$SO_3Na$ concentration has dramatically increased the solubilization ratio from around 11 to 25. This increase in solubilization ratio has decreased the IFT value (calculated from equation (1)) from 0.0024793 for the system UTMN-131 to 0.00048 for the system UTMN-137.

TABLE 4A

Phase behavior data recording sheet.

| Experiment | 0.33% C32—7PO—10EO—SO4, 0.33% C15-18 IOS, 0.33% C32—7BO—7PO—25EO—SO4, 0.5% TEGBE, 3.75% EDTA Na4 | | | | |
|---|---|---|---|---|---|
| Hydrocarbon | Crude oil | | | | |
| Surfactant | C32—7PO—10EO—SO4 | Hydrocarbon Density | g/cc | Typical hydrocarbon Densities: | |
| Co-Surfactant(1) | Petrostep S2 + C32—7B0—7PO—25EO—SO4 | Total Surfactant Conc. Total Alcohol Conc. | 1 wt % 0.5 wt % | Octane Decane | |
| Co-Solvent | TEGBE | Polymer Conc. | 0 wt % | | |
| Surfactant Conc. | 0.333 | Na2CO3 Conc. | 0 wt % | | |
| Co-surf(1) Conc. | 0.667 wt % | WOR | 1 | Mixed: Aug. 28, 2009 | Extended scan |
| t-pent Conc. | wt % | | | | |

TABLE 4A-continued

Phase behavior data recording sheet.

| alkali | 3.75% EDTA Na4 | wt % | Temperature | 100 Celcius |
| --- | --- | --- | --- | --- |
| NaCl:CaCl Ratio | | | Tube Size | 5 mL |

| Salinity (% of SUTIB) | TDS in ppm | Aqueous Level | Hydro-carbon Level | Top of emulsion | Top Interface | Bottom Interface | Bottom of emulsion | Type | Volume of Oil Solublized (cc) |
| --- | --- | --- | --- | --- | --- | --- | --- | --- | --- |
| | | Sep. 2, 2009 | 5 | days | | | | | |
| 50.00% | 28909 | 3.00 | 0.9 | | 2.90 | | | I | 0.10 |
| 60.00% | 34690 | 2.92 | 0.9 | | 2.81 | | | I | 0.11 |
| 70.00% | 40472 | 3.00 | 0.9 | | 2.90 | | | I | 0.10 |
| 80.00% | 46254 | 2.93 | 0.9 | | 2.81 | | | I | 0.12 |
| 90.00% | 52035 | 2.92 | 0.9 | | | | | I | 2.92 |
| 100.00% | 57817 | 2.94 | 0.9 | | 2.66 | 3.20 | | III | 0.28 |
| 110.00% | 63599 | 2.94 | 0.9 | | 2.66 | 3.10 | | III | 0.28 |
| 120.00% | 69380 | 2.96 | 0.9 | | | 3.00 | | II | 2.96 |
| 130.00% | 75162 | 2.93 | 0.9 | | | 2.99 | | II | 2.93 |
| 140.00% | 80944 | 3.00 | 0.9 | | | | | I | 3.00 |
| | | Sep. 16, 2009 | 19 | days | | | | | |
| 50.00% | 28909 | 3.00 | 0.9 | | 2.86 | | | I | 0.14 |
| 60.00% | 34690 | 2.92 | 0.9 | | 2.79 | | | I | 0.13 |
| 70.00% | 40472 | 3.00 | 0.9 | | 2.84 | | | I | 0.16 |
| 80.00% | 46254 | 2.93 | 0.9 | | 2.79 | | | I | 0.14 |
| 90.00% | 52035 | 2.92 | 0.9 | | | | | I | 2.92 |
| 100.00% | 57817 | 2.94 | 0.9 | | 2.69 | 3.20 | | III | 0.25 |
| 110.00% | 63599 | 2.94 | 0.9 | | 2.66 | 3.10 | | III | 0.28 |
| 120.00% | 69380 | 2.96 | 0.9 | | | 3.00 | | II | 2.96 |
| 130.00% | 75162 | 2.93 | 0.9 | | | 2.96 | | II | 2.93 |
| 140.00% | 80944 | 3.00 | 0.9 | | | | | I | 3.00 |

| Salinity (% of SUTIB) | Volume of Water Solublized (cc) | Oil Sol. Ratio (cc/cc) | Water Sol. Ratio (cc/cc) | HC Sol. (mg/L) | Volume Fraction of Oil ($V_o$) | Volume Fraction of Microemulsion ($V_{me}$) | Volumn Fraction of Water ($V_w$) | $V_w + V_{me}$ |
| --- | --- | --- | --- | --- | --- | --- | --- | --- |
| 50.00% | | 5.0 | | 0 | 0.488 | 0.512 | 0.000 | 0.512 |
| 60.00% | | 5.3 | | 0 | 0.466 | 0.534 | 0.000 | 0.534 |
| 70.00% | | 5.0 | | 0 | 0.488 | 0.512 | 0.000 | 0.512 |
| 80.00% | | 5.8 | | 0 | 0.466 | 0.534 | 0.000 | 0.534 |
| 90.00% | | | | 0 | −0.220 | 1.220 | 0.000 | 1.220 |
| 100.00% | 0.26 | 13.6 | 12.6 | 0 | 0.429 | 0.132 | 0.439 | 0.571 |
| 110.00% | 0.16 | 13.6 | 7.8 | 0 | 0.429 | 0.107 | 0.463 | 0.571 |
| 120.00% | 0.04 | | 2.0 | NA | 0 | 0.512 | 0.488 | 1.000 |
| 130.00% | 0.06 | | 2.9 | NA | 0 | 0.510 | 0.490 | 1.000 |
| 140.00% | | | | 0 | | | | |
| 50.00% | | 7.0 | | 0 | 0.478 | 0.522 | 0.000 | 0.522 |
| 60.00% | | 6.2 | | 0 | 0.461 | 0.539 | 0.000 | 0.539 |
| 70.00% | | 8.0 | | 0 | 0.473 | 0.527 | 0.000 | 0.527 |
| 80.00% | | 6.8 | | 0 | 0.461 | 0.539 | 0.000 | 0.539 |
| 90.00% | | | | 0 | −0.220 | 1.220 | 0.000 | 1.220 |
| 100.00% | 0.26 | 12.1 | 12.6 | 0 | 0.437 | 0.124 | 0.439 | 0.563 |
| 110.00% | 0.16 | 13.6 | 7.8 | 0 | 0.429 | 0.107 | 0.463 | 0.571 |
| 120.00% | 0.04 | | 2.0 | NA | 0 | 0.512 | 0.488 | 1.000 |
| 130.00% | 0.03 | | 1.4 | NA | 0 | 0.502 | 0.498 | 1.000 |
| 140.00% | | | | 0 | | | | |

TABLE 4B

Phase behavior data recording sheet.

| Experiment | 0.33% C32—7PO—10EO—SO4, 0.33% C15-18 IOS, 0.58% C32—7BO—7PO—25EO—SO4, 0.5% TEGBE, 3.75% EDTA Na$_4$ | | | | |
| --- | --- | --- | --- | --- | --- |
| Hydrocarbon | Crude OiL | | | | |
| Surfactant | C32—7PO—10EO—SO4 | | Hydrocarbon Density | g/cc | Typical hydrocarbon Densities: |
| Co-Surfactant(1) | Petrostep S2 + C32—7BO—7PO—25EO—SO4 | | Total Surfactant Conc. Total Alcohol Conc. | 1.249 wt % 0.5 wt % | Octane Decane |
| Co-Solvent | TEGBE | | Polymer Conc. | 0 wt % | |
| Surfactant Conc. | 0.333 | | Na2CO3 Conc. | 0 wt % | |
| Co-surf(1) Conc. | 0.916 | wt % | WOR | 1 | Mixed: Sep. 8, 2009 Extended scan |
| t-pent Conc. | | wt % | | | |
| alkali | 3.75% EDTA Na4 | wt % | Temperature | 100 Celcius | |
| NaCl:CaCl Ratio | | | Tube Size | 5 mL | |

TABLE 4B-continued

Phase behavior data recording sheet.

| Salinity (% of SUTIB) | TDS in ppm | Aqueous Level | Hydro-carbon Level | Top of emulsion | Top Interface | Bottom Interface | Bottom of emulsion | Type | Volume of Oil Solublized (cc) |
|---|---|---|---|---|---|---|---|---|---|
| | | Sep. 24, 2009 | 16 | days | | | | | |
| 50.00% | 28909 | | 0.9 | | 2.99 | | | | |
| 60.00% | 34690 | 3.05 | 0.9 | | 2.91 | | | I | 0.14 |
| 70.00% | 40472 | 3.02 | 0.9 | | 2.60 | 3.55 | | III | 0.42 |
| 80.00% | 46254 | 3.00 | 0.9 | | 1.80 | 3.20 | | III | 1.20 |
| 90.00% | 52035 | 3.01 | 0.9 | | | | | I | 3.01 |
| 100.00% | 57817 | 3.05 | 0.9 | | | | | I | 3.05 |
| 110.00% | 63599 | 3.02 | 0.9 | | | | | I | 3.02 |
| 120.00% | 69380 | 3.03 | 0.9 | | | | | I | 3.03 |
| 130.00% | 75162 | 3.00 | 0.9 | | | | | I | 3.00 |
| 140.00% | 80944 | 3.00 | 0.9 | | | | | I | 3.00 |
| | | Oct. 9, 2009 | 31 | days | | | | | |
| 50.00% | 28909 | | 0.9 | | 2.95 | | | | |
| 60.00% | 34690 | 3.05 | 0.9 | | 2.90 | | | I | 0.15 |
| 70.00% | 40472 | 3.02 | 0.9 | | 2.55 | 3.80 | | III | 0.47 |
| 80.00% | 46254 | 3.00 | 0.9 | | 2.45 | 3.30 | | III | 0.55 |
| 90.00% | 52035 | 3.01 | 0.9 | | 2.30 | 3.20 | | III | 0.71 |
| 100.00% | 57817 | 3.05 | 0.9 | | | | | I | 3.05 |
| 110.00% | 63599 | 3.02 | 0.9 | | 2.60 | | | I | 0.42 |
| 120.00% | 69380 | 3.03 | 0.9 | | | | | I | 3.03 |
| 130.00% | 75162 | 3.00 | 0.9 | | | | | I | 3.00 |
| 140.00% | 80944 | 3.00 | 0.9 | | | | | I | 3.00 |

| Salinity (% of SUTIB) | Volume of Water Solublized (cc) | Oil Sol. Ratio (cc/cc) | Water Sol. Ratio (cc/cc) | HC Sol. (mg/L) | Volume Fraction of Oil ($V_o$) | Volume Fraction of Microemulsion ($V_{me}$) | Volumn Fraction of Water ($V_w$) | $V_w + V_{me}$ |
|---|---|---|---|---|---|---|---|---|
| 50.00% | | | | | | | | |
| 60.00% | | 5.7 | | 0 | 0.490 | 0.510 | 0.000 | 0.510 |
| 70.00% | 0.53 | 17.0 | 21.4 | 0 | 0.415 | 0.232 | 0.354 | 0.585 |
| 80.00% | 0.20 | 48.0 | 8.0 | 0 | 0.220 | 0.341 | 0.439 | 0.780 |
| 90.00% | | | | 0 | −0.220 | 1.220 | 0.000 | 1.220 |
| 100.00% | | | | 0 | −0.220 | 1.220 | 0.000 | 1.220 |
| 110.00% | | | | 0 | −0.220 | 1.220 | 0.000 | 1.220 |
| 120.00% | | | | 0 | −0.220 | 1.220 | 0.000 | 1.220 |
| 130.00% | | | | 0 | −0.220 | 1.220 | 0.000 | 1.220 |
| 140.00% | | | | 0 | | | | |
| 50.00% | | | | | | | | |
| 60.00% | | 6.2 | | 0 | 0.488 | 0.512 | 0.000 | 0.512 |
| 70.00% | 0.78 | 19.0 | 31.5 | 0 | 0.402 | 0.305 | 0.293 | 0.598 |
| 80.00% | 0.30 | 22.0 | 12.0 | 0 | 0.378 | 0.207 | 0.415 | 0.622 |
| 90.00% | 0.19 | 28.6 | 7.6 | 0 | 0.341 | 0.220 | 0.439 | 0.659 |
| 100.00% | | | | 0 | −0.220 | 1.220 | 0.000 | 1.220 |
| 110.00% | | | | 0 | 0.415 | 0.585 | 0.000 | 0.585 |
| 120.00% | | | | 0 | −0.220 | 1.220 | 0.000 | 1.220 |
| 130.00% | | | | 0 | 1 220 | 0.000 | 1 220 | |
| 140.00% | | | | 0 | | | | |

REFERENCES

U.S. Pat. No. 5,092,405: Alkoxylated surfactant system for heavy oil reservoirs.
U.S. Pat. No. 7,119,125: Bi-modal Guerbet alkoxy sulfate surfactants.
U.S. Patent Application No. 20080217064: Drilling fluid and methods.
U.S. Patent Application No. 20090270281: Use of surfactant mixtures for tertiary mineral oil extraction.

What is claimed is:

1. An anionic ether surfactant of the general formula (I)

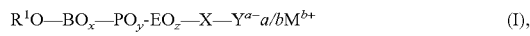

$$R^1O\text{---}BO_x\text{---}PO_y\text{---}EO_z\text{---}X\text{---}Y^{a-}{}_a/bM^{b+} \qquad (I),$$

wherein $R^1$ corresponds to an aliphatic, branched hydrocarbon group $C_nH_{2n+1}$ derived from a Guerbet alcohol (GA);
wherein n corresponds to the number of carbon atoms and ranges from 17 to 36,
wherein BO corresponds to a butoxy group;
wherein x corresponds to the number of butoxy groups and ranges from 2 to 25;
wherein PO corresponds to a propoxy group;
wherein y corresponds to the number of propoxy groups and ranges from 0 to 25;
wherein EO corresponds to a ethoxy group;
wherein z corresponds to the number of ethoxy groups and ranges from 0 to 70;
wherein X is selected from a single bond, an alkylene group with 1 to 10 carbon atoms or an alkenylene group with 2 to 10 carbon atoms;
wherein Y is an anionic group selected from the group of sulfate groups, sulfonate groups, carboxylate groups, phosphate groups or phosphonate groups;
wherein M is the counter ion to the anionic group,
wherein a corresponds to a number of 1 or 2,
wherein b corresponds to a number of 1 to 3.

2. The surfactant of claim 1, wherein M is selected from the group consisting of $H^+$, $Na^+$, $Mg$, $Ca^{2+}$, and $NH_4^+$.

3. The surfactant of claim 1, wherein n is 17, 18, 19, 20, 21, 22, 23, 24, 25, 26, 27, 28, 29, 30, 31, 32, 33, 34, 35, and 36.

4. The surfactant of claim 1, wherein x is 2, 3, 4, 8, 12, 16, 20, 22, 23, 24, and 25.

5. The surfactant of claim 1, wherein y is 0, 2, 4, 6, 8, 11, 14, 17, 21, and 25.

6. The surfactant of claim 1, wherein z is 0, 6, 8, 10, 12, 16, 20, 24, 32, 40, 48, 53, 57, 59, 62, 66, and 70.

7. The surfactant of claim 1, wherein the sum of y+z ranges from 0 to 95.

8. The surfactant of claim 1, wherein the anionic ether surfactant has a formula $R^1O—BO_7—PO_7-EO_{25}—SO_3^-$ 1/b $M^{b+}$, wherein $R^1$ is a hydrocarbon group $C_{32}H_{65}—$.

9. A method for making an anionic ether surfactant of the general formula (I)

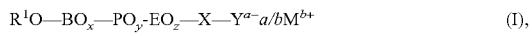

$$R^1O—BO_x—PO_y\text{-}EO_z—X—Y^{a-}a/bM^{b+} \quad (I),$$

from one or more branched Guerbet alcohols (GA) comprising the steps of:
providing one or more Guerbet alcohols (GA) having the general formula $R^1$—OH by dimerizing one or more alcohols $R^2$—OH in the presence of a base at a temperature from 175° C. to 275° C., wherein $R^2$—OH is an aliphatic, linear or branched alcohol and wherein the number of carbon atoms in $R^2$ is 6 to 18;
butoxylating the one or more GA with x butylene oxide (BO) units to form a butoxylated GA,
alkoxylating the one or more butoxylated GA with y propylene oxide (PO) units and z ethylene oxide (EO) units or both; and
converting the terminal OH-group of the alkoxylated GA thus obtained to the terminal group $—X—Y^{a-}$ a/b $M^{b+}$,
wherein $R^1$ corresponds to an aliphatic, branched hydrocarbon group $C_nH_{2n+1}$ derived from a Guerbet alcohol (GA);
wherein n corresponds to the number of carbon atoms and ranges from 17 to 36,
wherein BO corresponds to a butoxy group;
wherein x corresponds to the number of butoxy groups and ranges from 2 to 25;
wherein PO corresponds to a propoxy group;
wherein y corresponds to the number of propoxy groups and ranges from 0 to 25;
wherein EO corresponds to a ethoxy group;
wherein z corresponds to the number of ethoxy groups and ranges from 0 to 70;
wherein X is selected from a single bond, an alkylene group with 1 to 10 carbon atoms or an alkenylene group with 2 to 10 carbon atoms;
wherein Y is an anionic group selected from the group of sulfate groups, sulfonate groups, carboxylate groups, phosphate groups or phosphonate groups;
wherein M is the counter ion to the anionic group,
wherein a corresponds to a number of 1 or 2,
wherein b corresponds to a number of 1 to 3.

10. The method of claim 9, wherein n is 17, 18, 19, 20, 21, 22, 23, 24, 25, 26, 27, 28, 29, 30, 31, 32, 33, 34, 35, and 36.

11. The method of claim 9, wherein x is 2, 3, 4, 8, 12, 16, 20, 22, 23, 24, and 25.

12. The method of claim 9, wherein y is 0, 2, 4, 6, 8, 11, 14, 17, 21, and 25.

13. The method of claim 9, wherein z is 0, 6, 8, 10, 12, 16, 20, 24, 32, 40, 48, 53, 57, 59, 62, 66, and 70.

14. The method of claim 9, wherein M is selected from the group consisting of $H^+$, $Na^+$, $K^+$, $Mg^+$, $Ca^{2+}$, and $NH_4^+$.

15. The method of claim 9, wherein the anionic ether surfactant of formula (I) has a formula $R^1O—BO_7—PO_7\text{-}EO_{25}—SO_3^-$1/b $M^{b+}$, wherein $R^1$ is a hydrocarbon group $C_{32}H_{65}—$.

16. The method of claim 9, wherein the yield in course of the Guerbet reaction is 85% to less than 100%, thus obtaining a mixture which comprises the Guerbet alcohol $R^1$—OH with the remainder being the monomer alcohol $R^2$—OH and wherein the mixture thus obtained is used for the alkoxylation following the Guerbet condensation.

17. The method of claim 9, wherein the base comprises NaOH or KOH.

18. The method of claim 9, wherein the yield in course of the Guerbet reaction is 85%, 86%, 87%, 88%, 89%, 90%, 91%, 92%, 93%, 94%, 95%, 96%, 97%, 98%, and 99%.

19. The method of claim 9, wherein the GA is branched at near mid-point of the carbon chain.

20. The method of claim 9, wherein the Guerbet reaction is carried out at a temperature range of about 175° C. to 275° C.

21. The method of claim 9, wherein the Guerbet reaction is carried out at 175° C., 190° C., 200° C., 220° C., 230° C., 240° C., 250° C., and 275° C.

22. The method of claim 9, wherein the Guerbet reaction is carried out at 230° C.

23. A composition comprising:
at least one or more surfactants, wherein at least one or more of the surfactants is an anionic ether surfactant have a general formula (I)

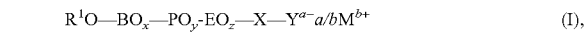

$$R^1O—BO_x—PO_y\text{-}EO_z—X—Y^{a-}a/bM^{b+} \quad (I),$$

wherein $R^1$ corresponds to an aliphatic, branched hydrocarbon group $C_nH_{2n+1}$ derived from a Guerbet alcohol (GA);
wherein n corresponds to the number of carbon atoms and ranges from 17 to 36,
wherein BO corresponds to a butoxy group;
wherein x corresponds to the number of butoxy groups and ranges from 2 to 25;
wherein PO corresponds to a propoxy group;
wherein y corresponds to the number of propoxy groups and ranges from 0 to 25;
wherein EO corresponds to a ethoxy group;
wherein z corresponds to the number of ethoxy groups and ranges from 0 to 70;
wherein X is selected from a single bond, an alkylene group with 1 to 10 carbon atoms or an alkenylene group with 2 to 10 carbon atoms;
wherein Y is an anionic group selected from the group of sulfate groups, sulfonate groups, carboxylate groups, phosphate groups or phosphonate groups;
wherein M is the counter ion to the anionic group,
wherein a corresponds to a number of 1 or 2,
wherein b corresponds to a number of 1 to 3,
one or more alkalinity generating agents; and
a solvent; wherein the one or more anionic ether surfactants, the one or more alkalinity generating agents are dissolved in the solvent.

24. The composition of claim 23, wherein M is selected from the group consisting of $H^+$, $Na^+$, $K^+$, $Mg^+$, $Ca^{2+}$, and $NH_4^+$.

25. The composition of claim 23, wherein the one or more anionic ether surfactants of formula (I) are selected from the group consisting of $C_{32}H_{65}O—BO_7—PO_7\text{-}EO_{25}—SO_3^-$1/b $M^{b+}$, $C_{32}H_{65}O—BO_x—PO_7\text{-}EO_6—SO_3^-$1/b $M^{b+}$, $C_{20}H_{41}O—BO_x—PO_7\text{-}EO_{10}—SO_3^-$1/b $M^{b+}$, wherein x corresponds to the number of butoxy groups and ranges from 2 to 25.

26. The composition of claim 23, wherein the composition furthermore comprises surfactants selected from sulfate, sulfonate, carboxylate anion based surfactants, ether sulfates, ethoxy sulfates, propoxy sulfates, perfluorooctanoate (PFOA or PFO), perfluorooctanesulfonate (PFOS), sodium dodecyl sulfate (SDS), ammonium lauryl sulfate, alkyl sulfate salts, sodium lauryl ether sulfate (SLES), alkyl benzene sulfonate, soaps, and fatty acid salts.

27. The composition of claim 23, wherein the one or more alkalinity generating agents comprise alkali earth metal hydroxides, NaOH, KOH, LiOH, ammonia, $Na_2CO_3$, $NaHCO_3$, Na-metaborate, sodium silicate, and/or sodium orthosilicate, with or without $EDTANa_4$ or polycarboxylates or any combinations thereof.

28. The composition of claim 23, wherein the solvent comprises water, hard brine, hard water, polymer containing solutions or any combinations thereof.

29. The composition of claim 23, wherein the composition is used in an alkaline-surfactant-polymer formulation for EOR applications.

30. The composition of claim 23, wherein the composition contains 0.1%, 0.15%, 0.2%, 0.25% 0.3%, 0.35%, 0.4%, 0.45%, 0.5%, and so on of the one or more alkalinity generating agents.

31. The composition of claim 23, wherein n is 17, 18, 19, 20, 21, 22, 23, 24, 25, 26, 27, 28, 29, 30, 31, 32, 33, 34, 35, and 36.

32. The composition of claim 23, wherein x is 2, 3, 4, 8, 12, 16, 20, 22, 23, 24, and 25.

33. The composition of claim 23, wherein y is 0, 2, 4, 6, 8, 11, 14, 17, 21, and 25.

34. The composition of claim 23, wherein z is 6, 8, 10, 12, 16, 20, 24, 32, 40, 48, 53, 57, 59, 62, 66, and 70.

35. The composition of claim 23, wherein the composition is adapted for enhanced oil recovery (EOR), environmental ground water cleanup, and other surfactant-based operations.

* * * * *